United States Patent
Boniface et al.

(10) Patent No.: US 10,894,837 B2
(45) Date of Patent: Jan. 19, 2021

(54) MMP9 INHIBITORS AND USES THEREOF IN THE PREVENTION OR TREATMENT OF A DEPIGMENTING DISORDER

(71) Applicants: UNIVERSITE DE BORDEAUX, Bordeaux (FR); INSERM (INSTITUT NATIONAL DE LA SANTE ET DE LA RECHERCHE MEDICALE), Paris (FR); CENTRE HOSPITALIER UNIVERSITAIRE DE BORDEAUX, Talence (FR)

(72) Inventors: Katia Boniface, Marignac (FR); Julien Seneschal, Bordeaux (FR); Nesrine Boukhedouni, Bordeaux (FR); Clement Jacquemin, Lanton (FR); Francois-Xavier Bernard, Saint Maurice-la-Clouere (FR)

(73) Assignees: UNIVERSITÉ DE BORDEAUX, Bordeaux (FR); INSERM (INSTITUT NATIONAL DE LA SANTE ET DE LA RECHERCHE MEDICALE), Paris (FR); CENTRE HOSPITALIER UNIVERSITAIRE DE BORDEAUX, Talence (FR)

( * ) Notice: Subject to any disclaimer, the term of this patent is extended or adjusted under 35 U.S.C. 154(b) by 0 days.

(21) Appl. No.: 16/469,665

(22) PCT Filed: Dec. 15, 2017

(86) PCT No.: PCT/EP2017/083182
§ 371 (c)(1),
(2) Date: Jun. 14, 2019

(87) PCT Pub. No.: WO2018/109222
PCT Pub. Date: Jun. 21, 2018

(65) Prior Publication Data
US 2019/0359730 A1 Nov. 28, 2019

(30) Foreign Application Priority Data
Dec. 16, 2016 (EP) .................................. 16306719

(51) Int. Cl.
| | | |
|---|---|---|
| *A61P 17/00* | (2006.01) | |
| *A61K 31/00* | (2006.01) | |
| *C07K 16/40* | (2006.01) | |
| *G01N 33/53* | (2006.01) | |
| *A61K 31/166* | (2006.01) | |

(52) U.S. Cl.
CPC ............ *C07K 16/40* (2013.01); *A61K 31/166* (2013.01); *G01N 33/53* (2013.01); *C07K 2317/56* (2013.01); *C07K 2317/76* (2013.01); *C12Y 304/24035* (2013.01)

(58) Field of Classification Search
CPC .............................. A61P 17/00; A61K 31/166
See application file for complete search history.

(56) References Cited

FOREIGN PATENT DOCUMENTS

| WO | WO 2006/037513 | 4/2006 |
| WO | WO 2010/093607 | 8/2010 |
| WO | WO 2016/023972 | 2/2016 |

OTHER PUBLICATIONS

Kumar et al., "Altered levels of Ets-1 transcription factor and matrix metalloproteinases in melanocytes from patients with vitiligo," Br. J. Dermatol. Aug. 2011;165(2):285-91. PMID: 21428970. (Year: 2011).*
Levin et al. "The discovery of anthranilic acid-based MMP inhibitors. Part 2: SAR of the 5-position and P1(1) groups," Bioorg. Med. Chem. Lett. Aug. 20, 2001;11(16):2189-92. PMID: 11514167. (Year: 2001).*
Lan et al., "FK506 promotes melanocyte and melanoblast growth and creates a favourable milieu for cell migration via keratinocytes: possible mechanisms of how tacrolimus ointment induces repigmentation in patients with vitiligo," Br. J. Dermatol. Sep. 2005;153(3):498-505. PMID: 16120133. (Year: 2005).*
Faas, L. et al. "In vivo evaluation of piperine and synthetic analogues as potential treatments for vitiligo using a sparsely pigmented mouse model" *British Journal of Dermatology*, 2008, pp. 941-950, vol. 158, No. 5.
Goffin, L. et al. "Anti-MMP-9 Antibody: A Promising Therapeutic Strategy for Treatment of Inflammatory Bowel Disease Complications with Fibrosis" *Inflamm Bowel Dis.*, Sep. 2016, pp. 2041-2057, vol. 22, No. 9.
Marshall, D. C. et al. "Selective Allosteric Inhibition of MMP9 Is Efficacious in Preclinical Models of Ulcerative Colitis and Colorectal Cancer" *PLOS ONE*, May 11, 2015, pp. 1-26, vol. 10, No. 5.
Wagner, R. Y. et al. "Altered E-Cadherin Levels and Distribution in Melanocytes Precede Clinical Manifestations of Vitiligo" *Journal of Investigative Dermatology*, 2015, pp. 1810-1819, vol. 135, No. 7.
Hwang, Y. P. et al. "Suppression of phorbol-12-myristate-13-acetate-induced tumor cell invasion by piperine via the inhibition of PKCα/ERK1/2-dependent matrix metalloproteinase-9 expression" *Toxicology Letters*, May 30, 2011, pp. 9-19, vol. 203, No. 1.

(Continued)

*Primary Examiner* — Theodore R. West
(74) *Attorney, Agent, or Firm* — Saliwanchik, Lloyd & Eisenschenk

(57) ABSTRACT

The invention relates to the field of therapy, in particular dermatology. Inventors herein identify for the first time inhibitors of matrix metalloproteinase-9 (MMP9) as active molecules for use for preventing, treating or alleviating skin depigmenting disorders in a subject in need thereof, and describe compositions and kits comprising such inhibitors as well as uses thereof. Inventors further describe a method for screening pharmaceutically active molecules suitable for preventing, treating or alleviating a depigmenting disorder as well as methods for evaluating the efficacy of a depigmenting disorder treatment involving an inhibitor of MMP9 or for monitoring the course of depigmenting disorder in a subject exposed to such a treatment.

Figure 1:
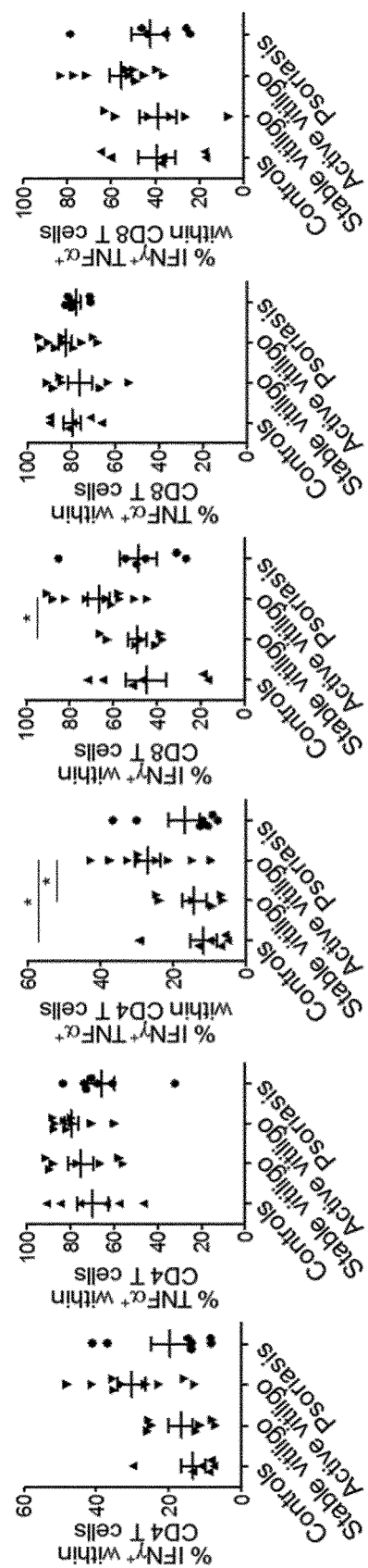

15 Claims, 13 Drawing Sheets
Specification includes a Sequence Listing.

(56) References Cited

OTHER PUBLICATIONS

Written Opinion in International Application No. PCT/EP2017/083182, dated Mar. 20, 2018, pp. 1-8.

* cited by examiner

A

B

Spearman r = 0.2040
P=0.0462

A   Skin

B   RHPE

A

B

MMP9 INHIBITORS AND USES THEREOF IN THE PREVENTION OR TREATMENT OF A DEPIGMENTING DISORDER

CROSS-REFERENCE TO RELATED APPLICATION

This application is the U.S. national stage application of International Patent Application No. PCT/EP2017/083182, filed Dec. 15, 2017.

The Sequence Listing for this application is labeled "Seq-List.txt" which was created on Jun. 6, 2019 and is 11 KB. The entire content of the sequence listing is incorporated herein by reference in its entirety.

The invention relates to the field of therapy, in particular dermatology. Inventors herein identify for the first time inhibitors of matrix metalloproteinase-9 (MMP9) as active molecules for use for preventing, treating or alleviating skin depigmenting disorders, typically skin depigmentation, in a subject in need thereof, and describe compositions and kits comprising such inhibitors as well as uses thereof. Inventors further describe a method for screening pharmaceutically active molecules suitable for preventing, treating or alleviating a depigmenting disorder, typically skin depigmentation, as well as methods for evaluating the efficacy of a depigmenting disorder treatment involving an inhibitor of MMP9 or for monitoring the course of depigmenting disorder in a subject exposed to such a treatment.

BACKGROUND

Vitiligo is the most common skin depigmenting disorder. The estimated prevalence of vitiligo is around 0.5% to 1% of the world population. Both sexes are equally affected, and there are no apparent differences in rates of occurrence according to skin type or race. It is clinically characterized by symmetric and bilateral white macules, resulting from a loss of epidermal melanocytes, the pigment-producing cells.

Several mechanisms have been implicated to explain melanocyte disappearance, including genetic predisposition, environmental triggers (such as friction), metabolic alteration, and altered inflammatory and immune responses. Vitiligo is described as an acquired chronic depigmenting disorder of the skin which is associated with autoimmune components involving both CD4$^+$ and CD8$^+$ T cells. However the phenotype and contribution of effector memory T (TEM) cell subsets remain to date unclear and controversial due to the lack of extensive analysis in models of the disease.

Several inflammatory skin diseases/dermatosis such as psoriasis, atopic dermatitis, scleroderma, typically cutaneous scleroderma, hypomelanosis and leukotrichia, lead to, or are associated with depigmentation among other symptoms.

Vitiligo in particular is a stigmatizing disease with major social and psychological impact. Often seen as purely aesthetic, this disorder is indeed responsible for a major impairment of quality of life sometimes comparable to other chronic diseases such as depression. Moreover patients with vitiligo often display other chronic inflammatory disorders such as autoimmune thyroiditis, rheumatoid arthritis and inflammatory bowel diseases. However, despite its prevalence and impact, no specific curative intervention has been reported so far. To date, no treatment has demonstrated efficacy against depigmentation. In addition there is no treatment allowing the blockade of depigmentation or skin repigmentation, preferably definitive skin repigmentation. Current treatments have overall limited efficacy and include topical steroids or calcineurin inhibitors, systemic steroids and/or UV-light (Cochrane Database Syst Rev. 2015 Feb. 24; (2):CD003263. doi: 10.1002/14651858.CD003263.pub5. Interventions for vitiligo. Whitton M E1, Pinart M, Batchelor J, Leonardi-Bee J, Gonzales U, Jiyad Z, Eleftheriadou V, Ezzedine K., and JAMA. 2016 Oct. 25; 316(16):1708-1709. doi: 10.1001/jama.2016.12399. Interventions for Vitiligo. Ezzedine Kl, Whitton M2, Pinart M3.), all of which have potential long-term side-effects.

BRIEF DESCRIPTION OF THE INVENTION

Inventors herein identify matrix metalloproteinase-9 (MMP9) as a therapeutic target specifically involved in depigmenting disorders and describe for the first time inhibitors thereof as active molecules for use for preventing or treating a depigmenting disorder/for use in prevention or treatment of a depigmenting disorder, in particular a disorder inducing skin's depigmentation, typically skin depigmentation, in a subject in need thereof.

Objects herein described thus relate to an inhibitor of matrix metalloproteinase-9 (MMP9), or to a composition or kit comprising such an inhibitor, for use for preventing, treating or alleviating a depigmenting disorder/for use in prevention, treatment or alleviation of a depigmenting disorder, typically skin depigmentation, in a subject in need thereof. The composition and kit preferably comprise the inhibitor of MMP9 together with a pharmaceutically acceptable excipient, carrier or support.

Inventors in addition herein describe methods for the screening of modulatory molecules to identify new drugs of interest and prepare pharmaceutical compositions, in particular therapeutic compositions as well as compositions capable of preventing depigmentation, for example capable of preventing the loss of epidermal melanocytes and/or of stabilizing melanocytes to the basement membrane of the epidermis. A particular method herein described is a method for screening, typically in vitro or ex vivo, pharmaceutically active molecules suitable for preventing, treating or alleviating a depigmenting disorder, typically skin depigmentation, in a subject in need thereof, wherein the method comprises a step of evaluating the ability of the tested molecule to inhibit MMP9 expression or function, to inhibit both MMP9 and Janus kinases (JAK) expression or function, in particular the expression or function of a JAK selected from JAK1, JAK2, JAK3, TYK2 and any combination thereof to induce melanin production and/or melanocyte function, to cleave E-cadherin, to increase soluble E-cadherin expression, to increase cytoplasmic redistribution of E-cadherin, to relocalize membrane bound E-cadherin, and/or to stabilize melanocytes to the basement membrane of the epidermis, said ability(ies) indicating that the tested molecule is a pharmaceutically active molecule suitable for preventing, treating or attenuating a depigmenting disorder, typically skin depigmentation, in a subject in need thereof.

Also herein described is a method for evaluating the efficacy of a treatment involving an inhibitor of MMP9 for treating a depigmenting disorder, typically skin depigmentation, in a subject, wherein the method comprises a step of comparing, typically in vitro or ex vivo, the expression of soluble E-cadherin in a first biological sample taken from a subject at t0 to the expression of soluble E-cadherin in a second biological sample taken from said subject at t1, t1 being posterior to to, an increase of the expression of soluble E-cadherin in the sample taken at t1 being an indicator of the progression of the depigmenting disorder in said subject and a decrease of the expression of soluble E-cadherin in the sample taken at t1 being an indicator of the regression of the depigmenting disorder in said subject.

Further herein described is a method for monitoring, typically for monitoring in vitro or ex vivo, the course of a depigmenting disorder, typically skin depigmentation, in a subject exposed to a treatment involving an inhibitor of MMP9, comprising comparing the expression of soluble E-cadherin in a first biological sample from a subject identified as having a depigmenting disorder before any treatment thereof to the expression of soluble E-cadherin in a second biological sample of the same subject who has been exposed to a drug or composition for treating the depigmenting disorder, a decrease in the expression of soluble E-cadherin in the second biological sample being an indicator of efficacy of the drug or composition for treating or attenuating the depigmenting disorder, and an increase in the expression or an absence of modulation of the expression of soluble E-cadherin in the second biological sample being an indicator of inefficacy of the drug or composition for treating or attenuating the depigmenting disorder.

DETAILED DESCRIPTION OF THE INVENTION

The skin is a large and complex tissue providing a protective interface between an organism and its environment. Epidermis forms its external surface, and is mainly constituted of multiple layers of specialized epithelial cells named keratinocytes. Melanocytes are melanin-producing cells located in the bottom layer of the epidermis and are responsible for the production of melanin: the pigment primarily responsible for skin color. Skin can be injured by many different causes, including microorganisms, chemicals, behaviours, physical injury, ageing, U.V. irradiation, cancer, autoimmune or inflammatory diseases.

A loss of epidermal melanocytes and/or the detection of functional abnormalities of epidermal melanocytes (such as abnormalities of melanocyte adhesion to the basement membrane of epidermis, melanocytes proliferation's abnormalities, increase of inflammatory proteins secretion, abnormalities of melanin and/or melanosomes transfer to keratinocytes) are the pathogenic hallmarks of disorders associated with skin depigmentation. Vitiligo, the most common depigmenting disease is associated with complete loss of melanocytes. Factors involved in the initiation of vitiligo remain largely unknown, but likely include genetic predisposition and environmental triggers (such as friction). However, the mechanisms leading to the loss of melanocytes are still in debate. Several theories have been proposed. Melanocyte-intrinsic abnormalities in vitiligo leading to impaired melanocyte degeneration and/or proliferation support the hypothesis that the disease could be due to a primary defect of melanocytes. However, other observations strongly support the role of the autoimmune system, particularly in the chronic and progressive phases of vitiligo. Genome wide association studies have shown that 90% of vitiligo susceptibility loci encode components of the immune system. Furthermore, vitiligo is often associated with autoimmune diseases, and both innate and adaptive immune cells are found in patients' affected skin. Loss of melanocytes could result from cell destruction through melanocyte-specific cytotoxic immune responses (mainly through $CD8^+$ cells) and/or melanocyte detachment through a defective adhesion system, also called melanocytorrhagy. E-cadherin, which is the major mediator of human melanocytes adhesion in the epidermis, was recently shown to be absent or discontinuously distributed across melanocyte membranes of vitiligo patients. Such alteration is responsible for melanocytes detachment from the basal layer of the epidermis and their subsequent loss.

E-cadherin is a calcium-dependent single-pass type I transmembrane glycoprotein, member of the cadherin superfamily that is localized to the adherens junction and basolateral membrane in epithelial cells. The extracellular portion contains five extracellular cadherin domain repeats that bind calcium ions to form a stiffened linear molecule. The cytoplasmic domain interacts with the catenins and a variety of actin-binding proteins to anchor the cadherin-catenin complex, important for the actin cytoskeleton and modulation of intracellular signaling pathways. Cleavage of E-cadherin, induced by several proteases including matrix metalloproteinases MMP (MMP3, MMP7, MMP9 and MT1-MMP), A-desintegrin-and-metalloproteinases (ADAM10 and ADAM15), plasmin and kallicrein 7, converts the mature 120-kDa E-cad into an extracellular N-terminal 80-kDA fragment and an intra-cellular C-terminal 38-kDa fragment.

Inventors herein describe MMP9 as a therapeutic target specifically involved in skin depigmenting disorders and advantageously identify, for the first time, inhibitors thereof, as active molecules for use for preventing, treating or alleviating a depigmenting disorder, in particular a disorder inducing skin's depigmentation, typically skin depigmentation, in a subject in need thereof.

In the experimental part of the present description, inventors have demonstrated the infiltration of skin inflammatory T cells expressing TNFα and IFNγ in progressive vitiligo and the involvement of TNFα and IFNγ in melanocytes loss through increased matrix metalloproteinase-9 (MMP9) expression, which could lead to dysfunction of E-cadherin and to the release of soluble E-cadherin. Inventors in particular showed that TNFα upregulated expression of MMP9 gene in melanocytes, and that this effect was also surprisingly potentiated in the presence of IFNγ. In addition, they showed that TNFα upregulated expression of MMP9 gene in keratinocytes.

The matrix metalloproteinase (MMP) family consists of at least 23 structurally related, soluble or membrane bound zinc-dependent endopeptidases that are broadly involved in the remodelling of the extracellular matrix (ECM) and in the functional regulation of various bioactive molecules. All MMPs possess a prototype structure that includes a pro-domain that maintains the MMP in an inactive form and a catalytic domain that acts on a broad spectrum of extracellular matrix components.

Matrix metallopeptidase 9 (MMP-9), also known as 92 kDa type IV collagenase, 92 kDa gelatinase or gelatinase B(GELB), is a matrixin, a class of enzymes that belong to the zinc-metalloproteinases family involved in the degradation of the extracellular matrix. In humans the MMP9 gene encodes for a signal peptide, a propeptide, a catalytic domain with three inserted repeats of fibronectin type II domain followed by a C-terminal hemopexin-like domain.

Proteins of the MMP family are involved in the breakdown of extracellular matrix in normal physiological processes, such as embryonic development, reproduction, angiogenesis, bone development, wound healing, cell migration, learning and memory, as well as in pathological processes, such as arthritis, intracerebral hemorrhage, and metastasis. Most MMPs are secreted as inactive proproteins which are activated when cleaved by extracellular proteinases. The enzyme encoded by this gene degrades type IV and V collagens and other extracellular matrix proteins.

Inventors now reveal the role of MMP9 in depigmenting disorders, in particular in depigmenting disorders associated with inflammation, typically in skin depigmentation disorders, and describe for the first time the use of inhibitors of MMP9 for preventing, treating or alleviating a depigmenting disorder, typically skin depigmentation, in a subject in need thereof, or for preparing a pharmaceutical composition, typically a dermatological composition, for preventing, treating or alleviating such a depigmenting disorder in a subject in need thereof.

An inhibitor of matrix metalloproteinase-9 (MMP9) for use for preventing, treating or alleviating a depigmenting disorder in a subject in need thereof is advantageously herein described. This inhibitor of MMP9 is a direct inhibitor of MMP9. The terms "direct inhibitor" indicate that the inhibitor directly acts (exerts its inhibitory action) on MMP9, or in other words that the inhibitor does not act on MMP9 via an intermediate distinct compound.

In a preferred aspect, the MMP9 inhibitor(s) is/are used in the context of the invention in the absence of any MMP2 inhibitor.

In the context of the invention, the MMP9 inhibitor typically decreases or neutralizes a biological activity of MMP9. As indicated previously, this inhibitor of MMP9 is a direct inhibitor of MMP9. This means that the inhibitor typically directly decreases or neutralizes a biological activity of MMP9, or in other words, that the MMP9 decreased or neutralized biological activity is not the result of the action of an intermediate compound ("indirect inhibitor of MMP9") such as for example a compound inhibiting or reducing PKCα and/or ERK phosphorylation or NF-κB and/or AP-1 activation. In a particular aspect, the MMP9 inhibitor is not piperine (PIP).

The MMP9 inhibitor in particular typically stabilizes melanocytes to the basement membrane of the epidermis. In other words, thanks to said inhibitor, the melanocytes loss, typical of depigmenting disorders such as vitiligo, is either significantly reduced or no longer observed. The MMP9 inhibitor typically significantly reduces the number of "detached" melanocytes, i.e. of melanocytes which are detached from the basal layer of the epidermis and/or from neighboring/adjacent keratinocytes. In a typical skin which has been exposed to/treated with an inhibitor of MMP9, "detached" melanocytes represent the minority of present melanocytes, i.e. less than 50%, for example less than 40%, 30%, 20%, 10%, 5%, 4%, 3%, 2% or 1% of present melanocytes.

The number of melanocytes can be easily counted and the proportion of melanocytes detached from the basal layer can be easily determined by the skilled person using conventional microscopy and marking/labeling methods of the art.

Using such an inhibitor can in addition significantly decrease the percentage of dead (or apoptotic) melanocytes, in particular of disrupted melanocytes which are typically observed in diseased depigmented skin.

Using such an inhibitor preferably also treat skin depigmentation, typically and preferably favors skin repigmentation. An increase of the concentration of melanine (the pigment produced by melanocyte responsible for the skin coloration) can be easily observed and measured by the skilled person (Luna, L. G., ed. (1968) in Manual of the Histologic Staining Methods of the AFIP (McGraw-Hill, New York), pp. 104-105.; Proc Natl Acad Sci USA. 2004 Oct. 19; 101(42):15076-81. Epub 2004 Oct. 11. Melanin acts as a potent UVB photosensitizer to cause an atypical mode of cell death in murine skin. Takeuchi 51, Zhang W, Wakamatsu K, Ito S, Hearing V J, Kraemer K H, Brash D E.).

Preferably, the inhibitor of MMP9 in addition stabilizes the cutaneous barrier by strengthening keratinocytes contact and cell adhesion.

The MMP9 inhibitor's pharmaceutical action can further be confirmed by i) an increase of the expression of Melanocyte Master Transcription Factor (MITF), Tyrosinase (TYR), Cadherin-1 also known as E-cadherin (CDH1), Dopachrome tautomerase (DCT), Tyrosinase Related Protein 1 (TRP1), connective tissue growth factor (CCN2), nephroblastoma overexpressed (CCN3) and Discoidin Domain Receptor family, member 1 (DDR1) genes and/or proteins, preferably of the DCT gene or protein, ii) by a decrease of the expression of C-X-C Motif Chemokine Receptor 3 (CXCR3) ligands such as C-X-C Motif Chemokine ligand 9 (CXCL9) and C-X-C Motif Chemokine ligand 10 (CXCL10), or by ii) a decrease or an inhibition of the expression of interleukin-6 (IL6), tumor necrosis factor (TNF), in particular TNFα, and intercellular adhesion molecule-1 (ICAM-1) genes and/or proteins, in a biological skin sample (biopsy) of the subject.

Assessment of the expression of the herein above identified proteins or genes can be easily performed by the skilled person respectively by immunohistochemistry/immunofluorescence and real time PCR. Chemokines levels can also be assessed by ELISA in cell-free supernatants.

Examples of MMP9 inhibitors of interest are antibodies directed against MMP9, aptamers or spiegelmers directed against MMP9, inhibitory nucleic acid sequences directed against MMP9 and small molecules directed against MMP9.

In a particular embodiment, the MMP9 inhibitor is an anti-MMP9 antibody. The antibody may be a polyclonal or a monoclonal antibody, most preferably a monoclonal antibody. It may be of various classes (e.g., IgG, IgE, IgM, etc.). The antibody may be of various animal origin, or human or humanized or synthetic or recombinant. Furthermore, the term antibody also includes fragments and derivatives thereof, in particular fragments and derivatives of said monoclonal or polyclonal antibodies having substantially the same antigenic specificity. Antibody fragments include e.g., Fab, Fab'2, CDRs, etc. Derivatives include humanized antibodies, human antibodies, chimeric antibodies, polyfunctional antibodies, Single Chain antibodies (ScFv), etc. These may be produced according to conventional methods, including immunization of an animal and collection of serum (polyclonal) or spleen cells (to produce hybridomas by fusion with appropriate cell lines).

Methods of producing polyclonal antibodies from various species, including mice, rodents, primates, horses, pigs, rabbits, poultry, etc. are well known from the skilled person. Briefly, the antigen is combined with an adjuvant (e.g., Freud's adjuvant) and administered to an animal, typically by sub-cutaneous injection. Repeated injections may be performed. Blood samples are collected and immunoglobulins or serum are separated.

Methods of producing monoclonal antibodies from various species as listed above may be found, for instance, in Harlow et al., 1988 or in Kohler et al. 1975, incorporated herein by reference. Briefly, these methods comprise immunizing an animal with the antigen, followed by a recovery of spleen cells which are then fused with immortalized cells, such as myeloma cells. The resulting hybridomas produce the monoclonal antibodies and can be selected by limit dilutions to isolate individual clones. Antibodies may also be produced by selection of combinatorial libraries of immunoglobulins, as disclosed for instance in Ward et al. (Nature 341 (1989) 544).

Recombinant antibodies, or fragments or derivatives thereof, may be produced by methods known per se in the art, for example by recombination in a host cell, transformed with one or more vectors enabling the expression and/or secretion of the nucleotide sequences encoding the heavy chain or the light chain of the antibody. The vector generally contains a promoter, translation initiation and termination signals, and suitable transcriptional regulatory regions. It is stably maintained in the host cell and may optionally possess specific signals for secretion of the translated protein. These different components are selected and optimized by one of skill in the art according to the host cell used.

In a preferred embodiment, the anti-MMP9 antibody, fragment or derivative thereof is an antibody, fragment or derivative thereof which binds the human MMP9 protein (SEQ ID NO: 1). Specific examples of such antibodies include monoclonal antibodies. In a preferred embodiment, the anti-MMP9 antibody, fragment or derivative thereof is an antibody, fragment or derivative thereof which selectively binds MMP9, i.e. which typically does not bind a distinct MMP.

Other antibodies may be found or generated against a MMP9 protein and used in the present invention. It should be noted however that the use of antibodies that bind an epitope present in MMP9 and wherein said binding is at least partially displaced by a human MMP9 protein is particularly preferred as well as a fragment or derivative of such an antibody having the same antigen specificity.

In a particular embodiment, the MMP9 antibody is selected from those disclosed in WO2016/023972, WO2012/027721, WO2013/130078 and WO2016/023979. Preferably, the MMP9 antibody comprises a heavy chain variable region comprising the sequence of SEQ ID NO: 2, 3 or 4 and/or a light chain comprising the sequence of SEQ ID NO: 5.

In a particular embodiment, the MMP9 inhibitor is an anti-MMP9 aptamer. Aptamers are non-encoding single-stranded nucleic acid (DNA or RNA) that have the property of binding specifically to a desired target compound or molecule, and that have sufficient capacity for forming a variety of two- and three-dimensional structures and sufficient chemical versatility available within their monomers to act as ligands (form specific binding pairs) with virtually any chemical compound, whether monomeric or polymeric, with a high affinity, via Van der Walls, hydrogen and electrostatic bounds (Pendergrast P. S. et al., 2005). Molecules of any size or composition can serve as targets.

Aptamers embody both the affinity properties of monoclonal antibodies and single chain antibodies and the manufacturing ease similar to that of a small peptide. Animal studies have shown that aptamers and compounds of similar composition are well tolerated, exhibit low or no immunogenicity, and are thus suitable for repeated administration as therapeutic compounds (Floege et al., Am. J. Pathol. 1999, 154:169-179; Ostendorf et al., J. Clin. Invest. 1999, 104: 913-923).

Aptamers are identified using the Systematic Evolution of Ligands by Exponential Enrichment (SELEX) process [Tuerk C. and Gold L. (1990) Science 249: 505-510; Ellington A D and Szostak J W. (1990) Nature 346: 818-822]. A pool of oligonucleotides (1013 to 1015 different sequences) is mixed with the target and only those linked to the target are selected. These aptamers are then amplified and used in the following cycle. After 5 to 15 amplifications steps, high affinity aptamers are obtained (Rimmelle M., 2003; Chauveau F. and al, 2006). This technique is now robotized.

Peptide aptamers consist of a conformationally constrained antibody variable region displayed by a platform protein, such as E. coli Thioredoxin A that are selected from combinatorial libraries by two hybrid methods (Colas et al., Nature, 1996,380, 548-50).

In a particular embodiment, the MMP9 aptamer is selected from those disclosed in WO2015/101637.

The MMP9 inhibitor may also be an anti-MMP9 Spiegelmer. Spiegelmers have been disclosed for instance in WO98/08856. They are molecules similar to aptamers. However, Spiegelmers consist either completely or mostly of L-nucleotides rather than D-nucleotides in contrast to aptamers. Otherwise, particularly with regard to possible lengths of Spiegelmers, the same applies to Spiegelmers as outlined in connection with aptamers.

In another particular embodiment, the inhibitory nucleic acid sequence directed against MMP9, used in the context of the invention as the MMP9 inhibitor, is selected from an interferent RNA, an antisense RNA and an oligonucleotide blocking a splicing site directed against MMP9.

The term "interferent RNA" means any RNA that is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. RNA interference designates a phenomenon by which dsRNA specifically suppresses expression of a target gene at post-translational level. In normal conditions, RNA interference is initiated by double-stranded RNA molecules (dsRNA) of several thousands of base pair length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein et al., 2001). In mammalian cells, the siRNAs produced by Dicer are 21-23 bp in length, with a 19 or 20 nucleotides duplex sequence, two-nucleotide 3' overhangs and 5'-triphosphate extremities (Elbashir et al., 2001 a; Elbashir et al., 2001 b; Zamore et al., 2000). A number of patents and patent applications have described, in general terms, the use of siRNA molecules to inhibit gene expression, for example WO 99/32619, US 20040053876, US 20040102408 and WO 2004/007718.

The sequence of the mRNA of MMP9 being known, one skilled in the art is capable of designing oligonucleotides capable of inhibiting the translation. Alternatively, one skilled in the art may use commercially available oligonucleotides like vectors of shRNA (cf. for example catalogue reference TR311436) and the siRNAs marketed by Origene society (for example of catalogue reference SR320997). Interferent RNAs directed against MMP9 are also marketed by Novus Biologicals society (catalogue reference: H00004318-R01).

By "down-regulating the expression" is meant, for example, a decrease of 30%, 40%, 50%, 60%, 70%, 80%, 90% or 95% of the gene expression.

The antisense nucleic acid, or antisense RNA can be complementary to all or part of a sense nucleic acid encoding MMP9 e.g., complementary to the coding strand of a double-stranded cDNA molecule or complementary to an mRNA sequence, and is thought to interfere with the translation of the target mRNA. Preferably, the antisense nucleic acid is an RNA molecule complementary to a target mRNA encoding MMP9.

In another particular embodiment, the MMP9 inhibitor is a small molecule directed against MMP9. Small molecules refer in particular to small organic molecules with a molecular mass inferior to 1000 Da. Small molecules and other drug candidates can readily be obtained, for example, from combinatorial and natural product libraries and using methods known from the skilled person of the art. Furthermore, random peptide libraries, consisting of all possible combinations of amino acids, attached to a solid phase or in solution, may also be used to identify peptides that act as inhibitor. Preferred small molecules are selected from the group consisting of 2-[[(4-phenoxyphenyl)sulfonyl]methyl]-Thiirane (SB3CT, CAS 292605-14-2), 2-(N-benzyl-4-methoxyphenylsulfonamido)-5-((diethylamino)methyl)-N-hydroxy-3-methylbenzamide (ab 142180, CAS 1177749-58-4) and N-{2-[(2-methoxyphenyl)amino]-4'-methyl-4,5'-bi-1,3-thiazol-2'-yl}acetamide, for example from the group consisting of 2-[[(4-phenoxyphenyl)sulfonyl]methyl]-Thiirane (SB3CT, CAS 292605-14-2), 2-(N-benzyl-4-methoxyphenylsulfonamido)-5-((diethylamino)methyl)-N-hydroxy-3-methylbenzamide (ab 142180, CAS 1177749-58-4).

Preferably, the MMP9 inhibitor decreases or inhibits the number of "detached" melanocytes ("melanocytes loss") or in other words, stabilizes melanocytes to the basement membrane of the epidermis.

Preferred MMP9 inhibitors usable in the context of the invention are selected from an anti-MMP9 antibody, such as an anti-MMP9 antibody comprising a heavy chain variable region comprising, or consisting in, the sequence of SEQ ID NO: 2, 3 or 4, and/or a light chain comprising, or consisting in, the sequence of SEQ ID NO: 5, and a small molecule such as 2-[[(4-phenoxyphenyl)sulfonyl]methyl]-Thiirane, 2-(N-benzyl-4-methoxyphenylsulfonamido)-5-((diethylamino)methyl)-N-hydroxy-3-methylbenzamide or N-{2-[(2-methoxyphenyl)amino]-4'-methyl-4,5'-bi-1,3-thiazol-2'-yl}acetamide.

Other preferred MMP9 inhibitors usable in the context of the invention are the anti-MMP9 monoclonal antibodies GS-5745 (Andecaliximab) and CALY-001.

The depigmenting disorder, or skin depigmentation, can be associated to an inflammatory skin disease, the depigmenting disorder, or skin depigmentation, being typically a symptom of the inflammatory skin disease.

In the context of the invention, the depigmenting disorder or inflammatory skin disease is typically selected from vitiligo, psoriasis, atopic dermatitis, scleroderma, typically systemic sclerosis, preferably cutaneous scleroderma, hypomelanosis, and leukotrichia.

In a preferred embodiment, the depigmenting disorder is vitiligo.

Preferably, the depigmenting disorder, disease or dysfunctional state is not a depigmenting disorder, disease or dysfunctional state of genetic or infectious origin.

Psoriasis is a chronic inflammatory multisystem disease, with predominantly skin and joint manifestations, affecting approximately 2% of the population. Almost 90% of affected individuals have psoriasis vulgaris. The major manifestation of psoriasis is chronic inflammation of the skin. It is characterised by disfiguring, scaling and erythematous plaques that may be painful or often severely pruritic. Psoriasis is a chronic disease that waxes and wanes during a patient's life time. Plaque psoriasis is the most common form, affecting approximately 80% to 90% of patients. Plaque psoriasis manifests as well-defined, sharply demarcated, erythematous plaques varying in size from 1 cm to several centimeters. Patients may have involvement ranging from only few plaques to numerous lesions covering almost the entire body surface. The inflammatory response developed in psoriasis can lead to skin depigmentation according to the same ranging. This manifestation alters the patients' life quality in the same way vitiligo does, the unaesthetic manifestations leading to depressive disorder or social withdrawal. Moreover spontaneously occurring vitiligo can be associated with psoriasis.

Atopic dermatitis (AD) is a chronic relapsing inflammatory skin disorder that affects approximately 2% to 5% of the adult population in the western world. The disease involves complex combinatorial pathogenic effects, multiple susceptibility genes, environmental triggers and disruption of the epidermal barrier. Clinically, AD can result in impairment of skin function, with intense and bothering itching leading to considerable loss of sleep and poor quality of life that is usually associated with disease severity. The inflammatory response developed in atopic dermatitis can lead to skin depigmentation according to the same ranging. This manifestation alters the patients' life quality in the same way vitiligo does, the unaesthetic manifestations leading to depressive disorder or social withdrawal. Moreover spontaneously occurring vitiligo can be associated with atopic dermatitis.

Scleroderma is an inflammatory disease. There are two forms of the disease: i) localized scleroderma (called "morphea"), involves isolated patches of hardened skin with no internal involvement and ii) systemic scleroderma (also called "systemic sclerosis") comprising two subgroups based on the extent of skin involvement (herein generally identified as "cutaneous scleroderma"): the subgroups are diffuse cutaneous scleroderma and limited cutaneous scleroderma. Systemic sclerosis can be associated with progressive visceral organs defects, including the kidneys, heart, lungs and gastrointestinal tract. Skin manifestations are progressive skin tightness and induration and prominent skin pigmentary changes (both hyperpigmentation and hypopigmentation). Those skin manifestations, as discussed with psoriasis and vitiligo, are responsible for a major alteration of patients' quality of life.

In a preferred embodiment, the inflammatory skin disease is vitiligo.

The skin depigmentation observed in the context of psoriasis, AD or scleroderma may remain/subsist even if the subject has been (successfully) treated for the psoriasis, AD or scleroderma. The MMP9 inhibitor of the invention is typically for use to treat or alleviate such a depigmentation, and preferably allows or favors skin repigmentation, even more preferably definitive skin repigmentation.

In the context of the invention, the "subject" is an animal, typically a mammal. Examples of mammals include humans and non-human animals such as, without limitation, domesticated animals (e.g., cows, sheep, pigs, rabbits cats, dogs, and horses), non-human primates (such as monkeys), and rodents (e.g., mice and rats). The "subject" is preferably a human being, whatever its gender, age, race or sex.

In a particular embodiment, the subject is a patient, i.e. a subject suffering from, or diagnosed or identified as suffering from, a skin depigmentation, a depigmenting disorder, disease or dysfunctional state and/or of an inflammatory skin disease as herein identified, typically leading or already associated to a depigmenting disorder.

In another particular embodiment, the subject is a healthy subject or an apparently healthy subject considered "at risk of developing" such a depigmenting disorder, disease or dysfunctional state, in particular at risk of developing a depigmenting disorder, typically a skin depigmentation, in whom this has to be prevented.

In a further particular embodiment, the subject is a subject having a scar, a wound, a cut or an incision or has undergone a skin graft.

In particular, the invention relates to the use of a MMP9 inhibitor as herein described for preparing a composition for preventing, treating or attenuating a depigmenting disorder, disease or dysfunctional state as herein previously identified, typically a skin depigmentation. Also herein described is thus a composition, typically a pharmaceutical composition, in particular a dermatological composition, wherein the composition comprises an inhibitor of MMP9 as herein described, preferably in a therapeutically effective amount.

A "therapeutically affective amount" of MMP9 inhibitor(s) is an amount allowing the treatment, as herein defined, of a subject as herein described, in particular a mammal, preferably a human being.

The doses of the MMP9 inhibitor or pharmaceutical composition comprising such an inhibitor may be adjusted by the skilled person depending on the treated subject and will depend upon a variety of factors/conditions including the age, body weight, general health, sex and diet of the subject. Doses will also vary depending on the route of administration, the optional presence of an additional biologically active compound (as herein disclosed), etc. Preferably, the composition does not comprise a MMP2 inhibitor.

Selection comprises determination of a dose effective to produce one, preferably several, even more preferably all, of the MMP9 inhibitor's herein above described effects, preferably of a dose effective to produce repigmentation, without essentially causing toxicity. For example, it is well known by the skilled person of the art to start doses of the product at levels lower than those required to achieve the desired therapeutic effect and to gradually increase the dosage until the desired effect is achieved. It will be understood that the total daily usage of the product of the present invention will be decided by the attending physician within the scope of sound medical judgment. Doses indicated herein below are examples which can be easily adapted by the skilled person/physician.

When the subject is a mammal, preferably a human being, the pharmaceutical composition typically comprises from about 0.1 to 150 mg per kg of body weight of MMP9 inhibitor, preferably from about 0.1 to 50 mg per body weight, even more preferably from 1 to 50 mg per body weight, for example from 0.250 mg to 20 mg per body weight (typically in the context of continuous infusion).

The pharmaceutical composition can in addition comprise from 0.1 to 150 mg per kg of body weight of a JAK inhibitor.

Similarly to the herein described MMP9 inhibitor, such a composition is typically for use for preventing, treating or attenuating a depigmenting disorder in a subject in need thereof, in particular for preventing, treating or attenuating depigmentation or for repigmenting a depigmented skin in a subject in need thereof.

In a particular aspect, the described MMP9 inhibitor, or composition comprising such an inhibitor, is for use for improving the aesthetic appearance of a scar or skin graft. In such a context, the composition can be considered as a cosmetic composition.

In a particular embodiment, the pharmaceutical composition of the invention comprises several distinct inhibitors of MMP9, for example at least two or three distinct inhibitors of MMP9.

The herein described MMP9 inhibitor can be used alone or in combination with i) a distinct MMP9 inhibitor, ii) a distinct MMP inhibitor which is not a MMP9 inhibitor, for example an inhibitor of MMP2 (although it is not a preferred embodiment of the invention), MMP3, MMP7, MT1-MMP, ADAM10, or ADAM15, iii) with phototherapy, or iv) with a drug selected from a Janus kinase (JAK) inhibitor, a PDE4 inhibitor, a vitamin D derivative, a calcineurin inhibitor, a corticosteroid, methotrexate, hydroxychloroquine, an anti-TNF, anti-IL-17, anti-IL-23, anti-p40, anti-CXCR3, anti-CXCL9, anti-CXCL10, CTLA4Ig, plasmin and kallicrein 7, a WNT agonist, or a GSK3β (Glycogen synthase kinase 3 beta) antagonist.

In a particular aspect, the herein described MMP9 inhibitor can be used in combination with a WNT agonist, a GSK3β antagonist, a calcineurin inhibitor, methotrexate, a Janus kinase (JAK) inhibitor, a corticosteroid or phototherapy.

In another particular aspect, the herein described MMP9 inhibitor can be used in combination with a calcineurin inhibitor, a Janus kinase (JAK) inhibitor or phototherapy.

In another particular embodiment, the pharmaceutical composition of the invention thus comprises, in addition to the at least one MMP9 inhibitor, a drug selected from a JAK inhibitor, a vitamin D derivative, a calcineurin inhibitor and a corticosteroid.

Janus kinases (JAK) are a family of intracellular, nonreceptor tyrosine kinases that transduce cytokine-mediated signals via the JAK-STAT pathway. JAKs possess two near-identical phosphate-transferring domains. One domain exhibits the kinase activity, while the other negatively regulates the kinase activity of the first.

In a preferred embodiment, the JAK inhibitor is selected from a JAK1 inhibitor such as ruxolitinib or tofacitinib, a JAK2 inhibitor such as ruxolitinib, a JAK 3 inhibitor such as tofacitinib, a TYK2 inhibitor and any combination thereof.

In preferred embodiment, the vitamin D derivative is topical calcipotriol, corticosteroid is selected from a topical steroid (for example Clobetasol propionate, Betamethasone dipropionate, Bethamethasone valerate, hydrocortisone aceponate, Difluprednate, Fluticasone, Desonide) or a systemic steroid (for example prednisolone, methylprednisolone, prednisone, dexamethasone), the calcineurin inhibitor is preferably a topical calcineurin inhibitor (for example tacrolimus or pimecrolimus).

In a typical embodiment, the pharmaceutical composition of the invention comprises a pharmaceutically acceptable excipient, vehicle, carrier or support in addition to the inhibitor of MMP9. The term "pharmaceutically acceptable" means approved by a regulatory agency of the Federal or a state government or listed in the U.S. Pharmacopeia, or European Pharmacopeia or other generally recognized pharmacopeia for use in animals, and more particularly in humans.

A pharmaceutically acceptable excipient, vehicle, carrier or support, usable in the context of the present invention, is for example a saline, isotonic, buffered solution such as Mannitol 20%, optionally combined with stabilizing agents such as isogenic albumin or any other stabilizing protein, glycerol, etc., and also adjuvants such as polybrene or DEAE dextrans, etc.

Further herein described is a method for preventing, treating or attenuating a depigmenting disorder, disease or dysfunctional state, such as one of those herein described, typically a skin depigmentation, in a subject in need thereof, comprising a step of exposing the subject to an inhibitor of MMP9, alone or in combination with a distinct drug as herein described, or to a composition comprising such an inhibitor as herein described.

The terms "treatment" or "treat" refer to therapeutic intervention in an attempt to alter the natural course of the subject being treated, and can be performed either for preventive (prophylactic) or curative purpose. Desirable effects of treatment include, but are not limited to, preventing occurrence or recurrence of the disorder, disease, or dysfunctional state, attenuation or alleviation of symptoms, diminishment of any direct or indirect pathological consequences of the disorder, disease, or dysfunctional state, decreasing the rate of the disorder, disease, or dysfunctional state progression, and amelioration or palliation of the disease state. In preferred embodiments, compositions and methods of the invention are used to delay development of a depigmenting disorder, disease, or dysfunctional state, to slow its progression or to cure the depigmenting disorder, typically to repigment, preferably by definitive repigmentation, a depigmented skin or skin area.

A typical MMP9 inhibitor according to the present invention (therapeutic or prophylactic MMP9 inhibitor), or herein described composition comprising such an inhibitor, is compatible with exposure of, or administration, to a subject as herein described, in particular a mammal, preferably a human being, in particular by way of injection in the bloodstream (systemic injection), such as intra-venous or intra-arterial injection, by way of cutaneous or subcutaneous (i.e. topical) administration, by way of intramuscular administration, by way of oral (per os) or rectal administration, and/or by way of nasal administration.

In a preferred embodiment, the composition is formulated for topic (cutaneous or subcutaneous) administration. Such a composition is typically considered as a dermatological composition.

Compositions will be advantageously formulated according to methods known by the man of the art.

When administered per oral or perlingual route, the composition is for example in the form of coated or uncoated tablet, gelatin capsule, powder, pellet, suspension or oral solution. When administered by rectal route, the composition is for example in the form of a suppository. One such form for oral or rectal administration can be either with immediate release or with extended or delayed release. When administered by intranasal route, the composition is for example in aerosol or spray form.

As indicated previously, preferred compositions will be advantageously formulated for topical application to the skin. Preferably, the composition used in the present invention is in the form of an emulsion, of a cream, of a lotion type, of a gel, or of a solution. The composition may be more or less fluid and may be in the form of salves, emulsions, creams, milks, ointments, impregnated pads, syndets, solutions, gels, sprays or aerosols, foams, suspensions, lotions or sticks.

For example, the composition may be in the form of an optionally gelled, oily solution, an optionally two-phase dispersion of the lotion type, an emulsion obtained by dispersion of a fatty phase in an aqueous phase (O/W) or vice versa (W/O), or a triple emulsion (W/O/W or O/W/O) or a vesicular dispersion of ionic and/or non-ionic type. This topical composition may be in anhydrous form, in aqueous form or in the form of an emulsion. These compositions are prepared according to the usual methods. Preferably, a composition in the form of an emulsion obtained by dispersion of a fatty phase in an aqueous phase (0/W) is used.

Various protocols may be used for the exposure/administration, such as simultaneous or sequential exposure/administration of the MMP9 inhibitor and of any other additional molecule, compound or drug as herein described, single or repeated administration, etc., which may be adjusted by the skilled person.

Inventors in addition herein provide a method for evaluating the efficacy of a treatment involving an inhibitor of MMP9 for treating a depigmenting disorder, disease or dysfunction, typically a skin depigmentation, in a subject. The method comprises a step of comparing the expression of anyone of soluble E-cadherin, MMP9, CXCL9 and CXCL10, preferably E-cadherin or MMP9, in a first biological sample taken from a subject at t0 to the expression of soluble E-cadherin, MMP9, CXCL9 and CXCL10, preferably E-cadherin or MMP9, in a second biological sample taken from said subject at t1, an increase of the expression of anyone of soluble E-cadherin, MMP9, CXCL9 and CXCL10 in the sample taken at t1 being an indicator of the progression of the depigmenting disorder, typically of the progression of the skin depigmentation, in said subject and a decrease of the expression of anyone of soluble E-cadherin, MMP9, CXCL9 and CXCL10 in the sample taken at t1 being an indicator of the regression of the depigmenting disorder, typically of the regression of the skin depigmentation or of the progression of the skin repigmentation, in said subject. Preferably, the biological sample is a serum sample (cf. FIG. 9).

A particular method for evaluating the efficacy of a treatment involving an inhibitor of MMP9 for treating a depigmenting disorder in a subject comprises an additional step of clinically evaluating depigmentation of the subject using VETF (Vitiligo European Task Force—Pigment Cell Res. 2007 February; 20(1):27-35. The definition and assessment of vitiligo: a consensus report of the Vitiligo European Task Force. Taïeb Al, Picardo M; VETF Members) and/or VES (Vitiligo Extent Score) score(s) (Van Geel et al., J. Invest Dermatol. 2016) or the VASI (Vitiligo Area Severity Index—Arch Dermatol. 2004 June; 140(6):677-83. Parametric modeling of narrowband UV-B phototherapy for vitiligo using a novel quantitative tool: the Vitiligo Area Scoring Index. Hamzavi I1, Jain H, Mc Lean D, Shapiro J, Zeng H, Lui H).

Inventors further herein provide a method for monitoring in vitro or ex vivo the course of a depigmenting disorder, disease or dysfunction, typically of a skin depigmentation, in a subject exposed to a treatment involving an inhibitor of MMP9. This method comprises a step of comparing the expression of soluble E-cadherin in a first biological sample from a subject identified as having, or suspected of having, a depigmenting disorder, disease or dysfunction before any treatment thereof to the expression of soluble E-cadherin in a second biological sample of the same subject who has been exposed to a drug or composition for treating the depigmenting disorder, disease or dysfunction, a decrease in the expression of soluble E-cadherin in the second biological sample being an indicator of efficacy of the drug or composition for treating or attenuating the depigmenting disorder, disease or dysfunction, typically the skin depigmentation, and an increase in the expression or an absence of modulation of the expression of soluble E-cadherin in the second biological sample being an indicator of inefficacy of the drug or composition for treating or attenuating the depigmenting disorder, disease or dysfunction, typically the skin depigmentation.

Detection and measure of the expression of soluble E-cadherin can be performed using conventional methods of the art such as ELISA (cf. for example R&D systems).

Also herein described is a method for screening, typically for screening in vitro or ex vivo, pharmaceutically active molecules suitable for preventing, treating or alleviating a depigmenting disorder, typically for preventing, treating or alleviating a skin depigmentation or for allowing or favoring the repigmentation of a skin, in a subject in need thereof. This method comprises a step of evaluating the ability of the tested molecule to inhibit MMP9 expression or function, to inhibit both MMP9 and Janus kinases (JAK) expression or function, in particular the expression or function of a JAK selected from JAK1, JAK2, JAK3, TYK2 and any combination thereof to induce melanin production and/or melanocyte function, to cleave E-cadherin, to increase soluble E-cadherin expression, to increase cytoplasmic redistribution of E-cadherin, to relocalize membrane bound E-cadherin, and/or to stabilize melanocytes to the basement membrane of the epidermis, said ability(ies) indicating that the tested molecule is a pharmaceutically active molecule suitable for preventing, treating or attenuating a depigmenting disorder, typically for preventing, treating or alleviating a skin depigmentation or for allowing or favoring the repigmentation of a skin, in a subject in need thereof.

The screening method is typically performed on a cellular model of depigmenting disorder, such as vitiligo, typically on a cellular tridimensional model.

To evaluate the potential therapeutic effect of a test molecule, the localization of melanocyte within the epidermis can be assessed, typically the detached melanocytes and attached melanocytes present in the epidermis, in particular in the basal layer, can be respectively quantified, and compared to the condition where only TNFα and IFNγ are present (positive control of depigmentation). Evaluation/quantification of soluble E-cadherin levels and/or membrane bound E-cadherin expression and/or quantification of melanin content can also be assessed and compared to a positive control. E-cadherin expression in a skin sample is classically assessed by immunofluorescence, immunohistochemistry, or western blot. Soluble E-cadherin levels are classically determined by ELISA.

Such a method is adaptable to automated, high throughput screening of compounds.

The candidate (test) pharmacological molecules/agents can be derived from, for example, combinatorial peptide libraries, combinatorial chemical compound libraries, and natural products libraries. Generally, the screening methods involve assaying for molecules or compounds which decrease or inhibit the expression or activity of MMP9. Molecules which can be tested are thus preferably selected for example from monoclonal antibodies, aptamers, spiegelmers, inhibitory nucleic acid sequences, small molecules. In a particular example, these molecules are directed against MMP9. Convenient reagents for such assays are known in the art.

Typically, pluralities of assay mixtures are run in parallel with different agent concentrations to obtain a different response to the various concentrations. Typically, one of these concentrations serves as a negative control, i.e., at zero concentration of agent or at a concentration of agent below the limits of assay detection.

The use of a molecule or compound which decreases or inhibits the expression or activity of MMP9 identified with the described screening method for the preparation of a composition for preventing, treating or alleviating a depigmenting disorder, typically skin depigmentation, is also herein described.

The invention also relates to kits suitable for implementing the herein above described methods and uses.

The present invention in particular provides a kit comprising at least one inhibitor of MMP9 or composition comprising such an inhibitor, and at least one additional drug as herein above described, for example a JAK inhibitor. This kit can comprise as many distinct (optionally sterile) containers as there are products of interest in the kit.

Typically, the kit also comprises instructions for using the herein described MMP9 inhibitor(s) or composition(s) according to the disclosed methods and uses, for example information for the administration of the effective amount for preventing or treating a particular depigmenting disorder, typically a skin depigmentation.

More particularly herein disclosed are uses of anyone of the herein described products for preventing, treating or attenuating a depigmenting disorder, disease or dysfunctional state such as one of those herein described, typically vitiligo or a skin depigmentation, for studying the pathogenesis of such a depigmenting disorder, disease or dysfunctional state, for studying pigmentation/depigmentation mechanisms, or evaluating the therapeutic and/or modulatory property(ies) of a compound which may interact with MMP9. A "MMP9 modulator" designates any molecule modulating (activating or inhibiting), preferably inhibiting, MMP9 expression or function.

The examples, which follow, and their corresponding figures illustrate the invention without limiting the scope thereof.

FIGURES

FIG. 1. Prominent infiltration of skin inflammatory T cells expressing TNFα and IFNγ in progressive vitiligo. T cells were isolated from perilesional skin of patients with a progressive (n=10) or a stable vitiligo (n=6). Results were compared to healthy controls (n=6). Analysis of IFNγ, TNFα, or IFNγ/TNFα producing skin infiltrating CD4 and CD8 T cells by flow cytometry. Each symbol represents one specimen. The mean+s.e.m. is shown.*$p<0.05$, **$p<0.01$, using a Mann Whitney test.

Figure 2:
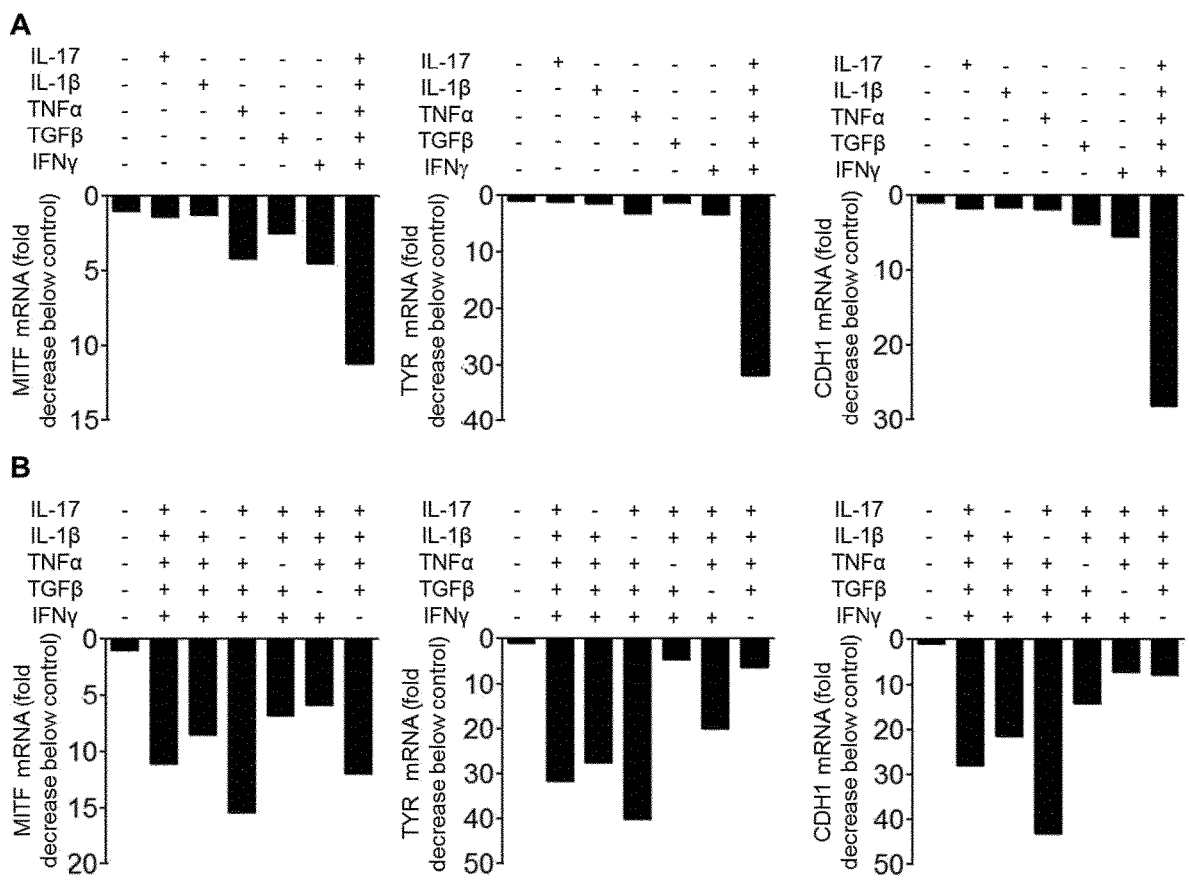

FIG. 2. TNFα and IFNγ: two major cytokines involved in melanocyte inhibition A-B. Primary cultures of normal human epidermal melanocytes were stimulated in the presence or absence of the indicated cytokines for 24 h (IL-17, IL-1β, TNFα, IFNγ: 20 ng/ml; TGFβ: 5 ng/ml). Real-time analysis of the indicated gene expression. Results are expressed as a fold decrease below control culture (no stimulation). GAPDH was used as a housekeeping gene. Data are representative of three independent experiments.

Figure 3:
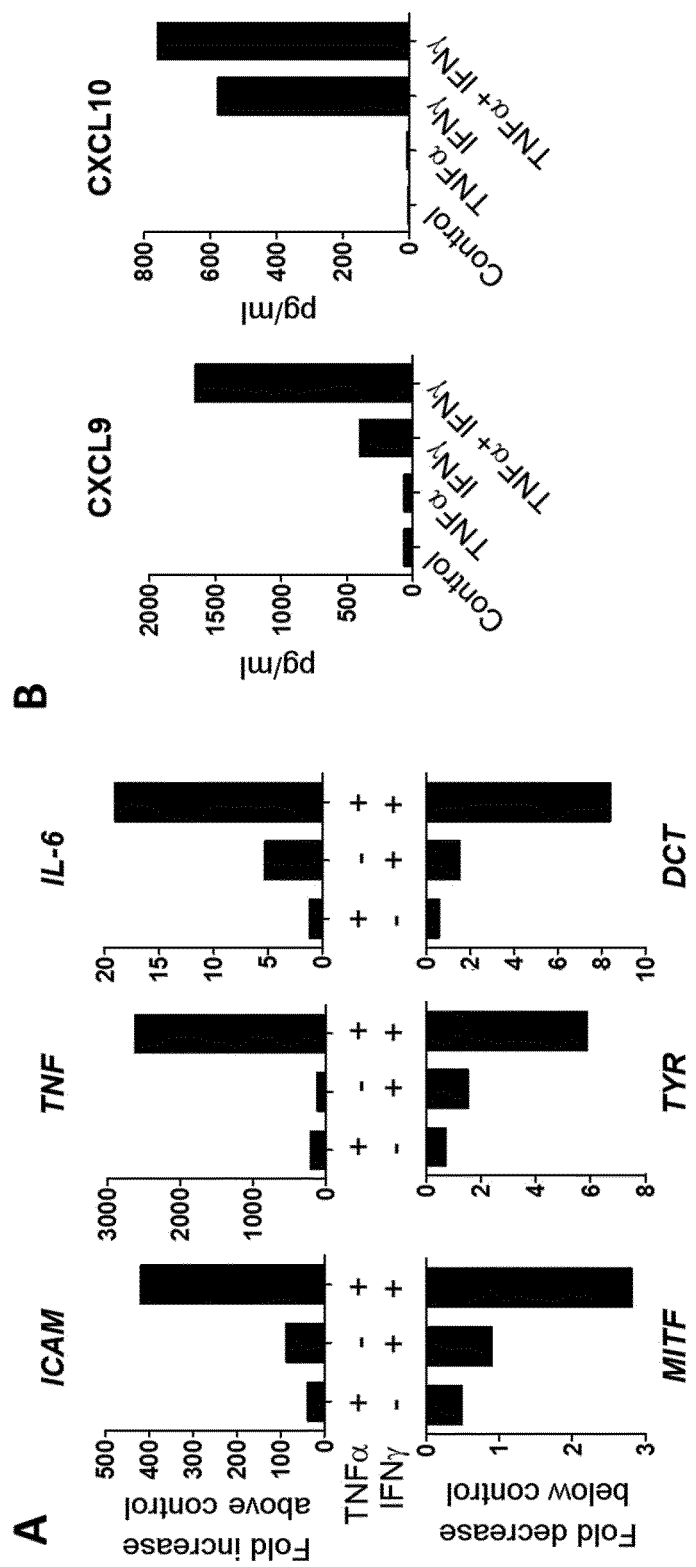

FIG. 3. Involvement of TNFα and IFNγ in the inflammatory response and depigmentation.

A-B. Primary cultures of normal human epidermal melanocytes were stimulated in the presence or absence of 20 ng/ml TNFα and/or IFNγ for 24 h (A) or 48 h (B). A. Real-time analysis of the indicated gene expression. Results are expressed as a fold increase above control culture (no stimulation) for upregulated genes (upper panel) or fold decrease below control culture for downregulated genes (lower panel). GAPDH was used as a housekeeping gene. B. Measurement of CXCL9 and CXCL10 secretion in cell-free supernatants by ELISA.

Figure 4:
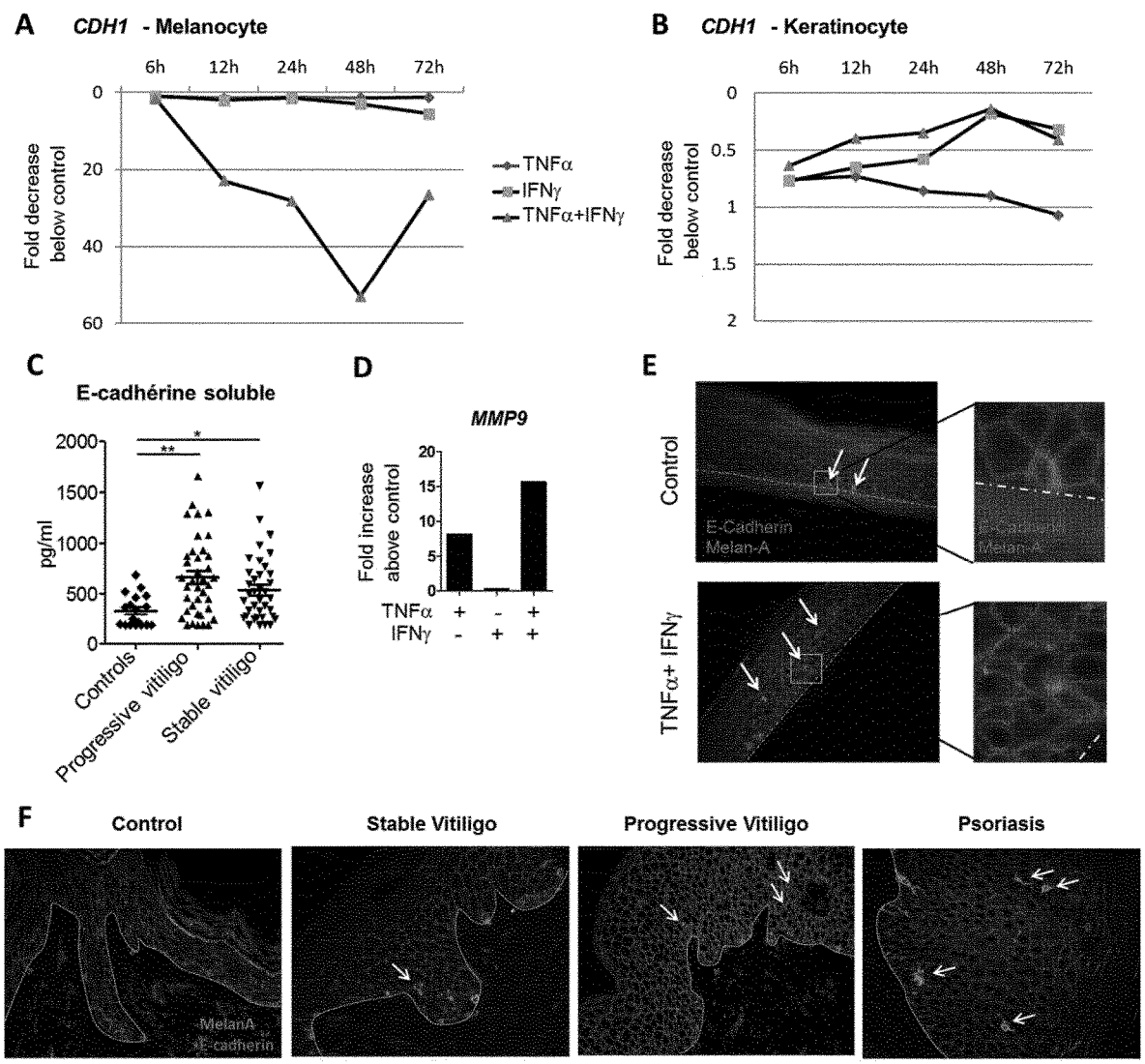

FIG. 4. Involvement of TNFα and IFNγ in the inflammatory response and melanocyte loss.

A-B. Primary cultures of normal human epidermal melanocytes (A) or keratinocytes (B) were stimulated in the presence or absence of 20 ng/ml TNFα and/or IFNγ for the indicated time. Real-time analysis of CDH1 gene expression. GAPDH was used as a housekeeping gene. C. Assessment of soluble E-cadherin levels in sera from healthy controls (n=20) or patients with a progressive (n=40) or a stable (n=40) vitiligo. Data are representative of three (A-D) or two (E) independent experiments. D. Real-time analysis of MMP9 gene expression in melanocytes treated 24 h with or without 20 ng/ml of TNFα and/or IFNγ. GAPDH was used as a housekeeping gene. E. Reconstructed human epidermis containing melanocytes were stimulated in the presence or absence of 20 ng/ml of TNFα and IFNγ for 24 h. Immunofluorescence microscopy analysis of melan-A (red) and E-cadherin (green) expression, Magnification 400×. E. Immunofluorescence microscopy analysis of melan-A (red) and E-cadherin (green) expression in healthy skin, perilesional skin of patients with stable or progressive vitiligo, and lesional psoiatic skin. Magnification 400×. White arrows show melanocytes that are detached from the basal layer of the epidermis.

Figure 5:
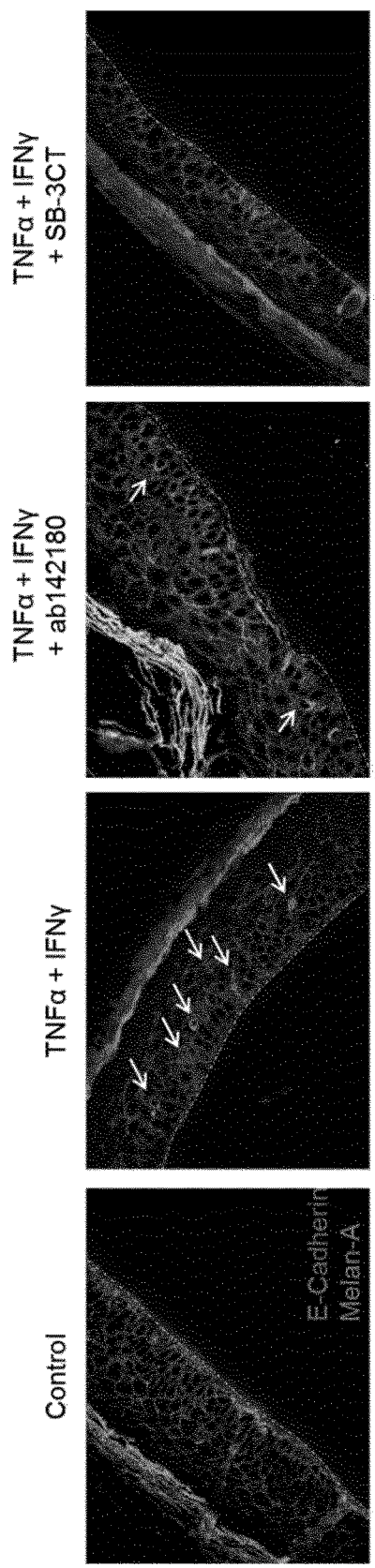

FIG. 5. TNFα, and IFNγ-induced melanocyte loss is mediated through MMP9.

Reconstructed human epidermis containing melanocytes were stimulated 24 h with or without 20 ng/ml of TNFα and IFNγ in the presence or absence of 10 μM of MMP9 inhibitor ab142180 or SB-CT. Immunofluorescence microscopy analysis of melan-A (red) and E-cadherin (green) expression, Magnification 400×. White arrows show melanocytes that are detached from the basal layer of the epidermis.

Figure 6:
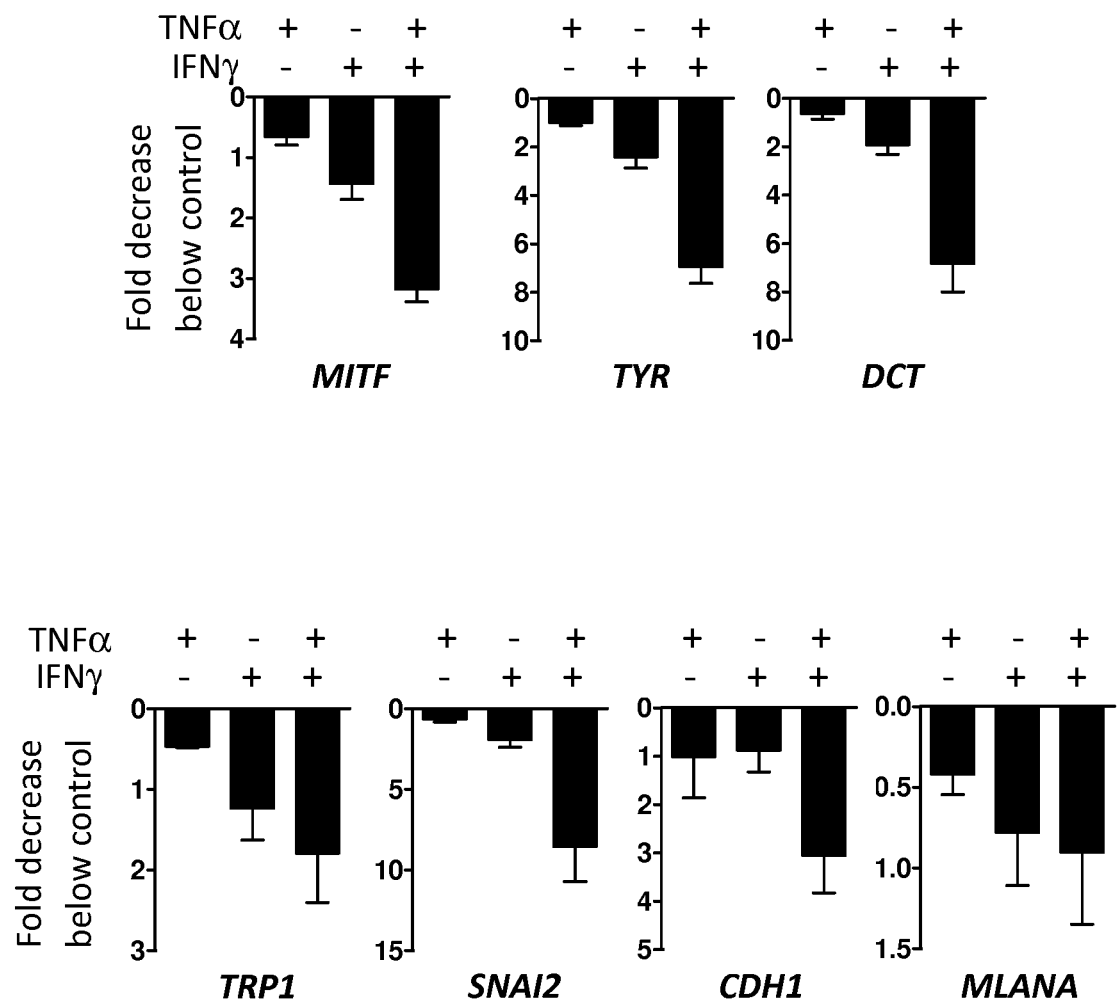

FIG. 6. Involvement of TNFα, and IFNγ in melanocyte loss.

Primary cultures of melanocytes were stimulated in the presence or absence of 20 ng/ml of TNFα and IFNγ. Analysis using quantitative RT-PCR of the expression of the indicated genes after 24 h of stimulation. The gene encoding GAPDH is used as a control gene. Results show the expression ratio between stimulated cells and control cells in the absence of cytokines [mean+standard error of the mean (SEM) of 3 experiments performed on 3 distinct samples]. Inventors observed a synergistic effect of the TNFα and IFNγ cocktail in the inhibition of genes encoding proteins involved in melanocyte function, melanogenesis and melanocytes adhesion.

Figure 7:
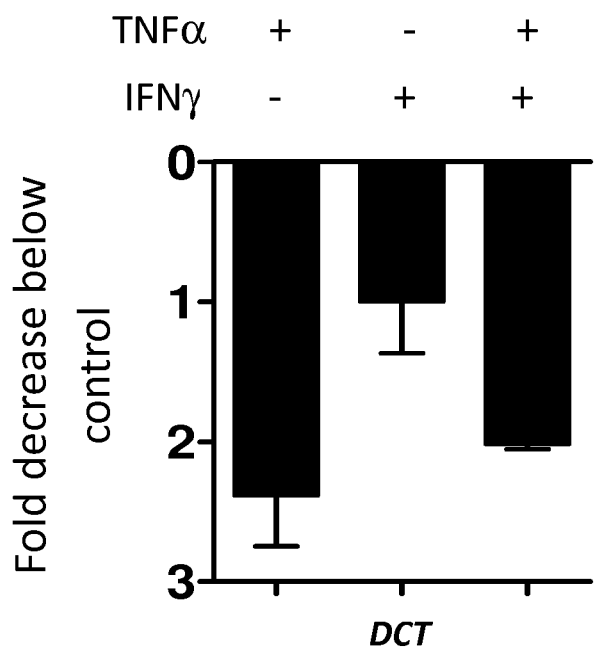

FIG. 7. Involvement of TNFα, and IFNγ in melanocyte loss.

Reconstructed human epidermis containing melanocytes were stimulated in the presence or absence of 20 ng/ml of TNFα and IFNγ. Analysis using quantitative RT-PCR of the DCT gene expression after 24 h of stimulation. The genes encoding GAPDH and β-glucuronidase are used as control genes. Results show the expression ratio between the stimulated epidermis and the control epidermis without cytokines [mean+standard error of the mean (SME) of 2 experiments performed on 2 different samples]. Inventors observe a DCT gene inhibition in presence of TNFα. This effect is not modified by addition of IFNγ.

Figure 8:
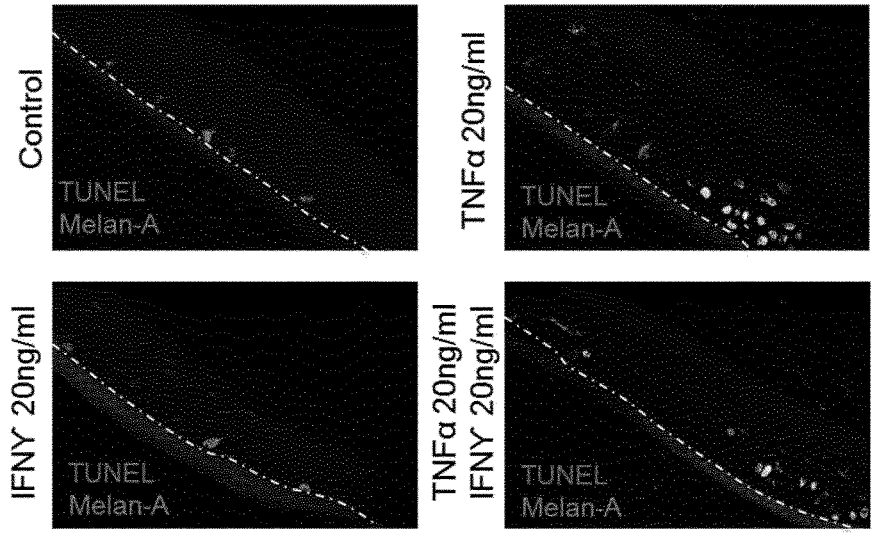
Figure 8:
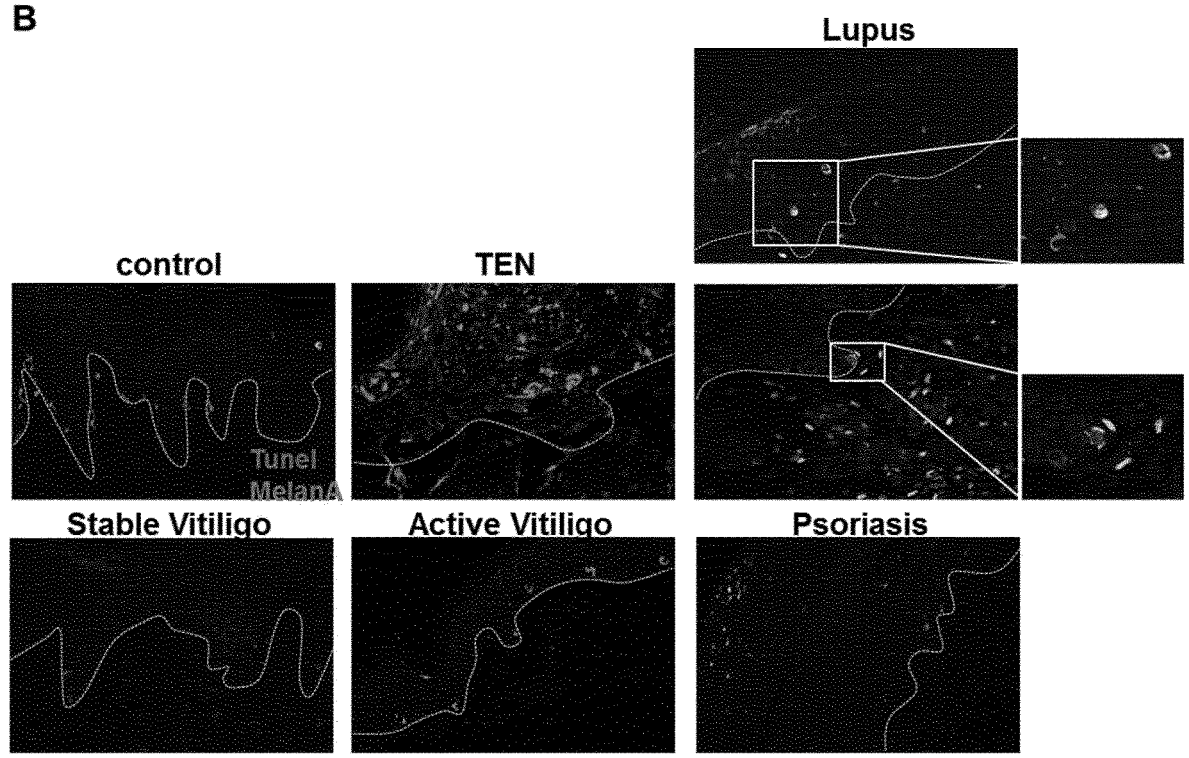

FIG. 8. Cell death is not a primary mechanism involved in melanocyte loss. (A-B). Reconstructed human epidermis containing melanocytes were stimulated in the presence or absence of 20 ng/ml of TNFα and IFNγ for 24 h. Analysis of Melan-A expression (red color reveals melanocytes) using immunofluorescence and detection of apoptotic cells (green) using TUNEL technique (results representative of 2 experiments performed on 2 distinct samples). Results show that TNFα and/or IFNγ have no effect on melanocytes apoptosis. A slight pro-apoptotic effect of TNFα on keratinocytes is observed. (B) Analysis of Melan-A expression (red color reveals melanocytes) using immunofluorescence and detection of apoptotic cells (green) using TUNEL technique in healthy skin (control), perilesional skin of patients with stable or progressive vitiligo, lesional skin of patients with psoriasis or lupus. Magnification 400×. TEN is a positive control for apoptosis. Results show that in vitiligo patients (with a stable or active disease), detached melanocytes do not enter apoptosis, emphasizing that melanocyte death is not the primary mechanism involved in their loss.

Figure 9:
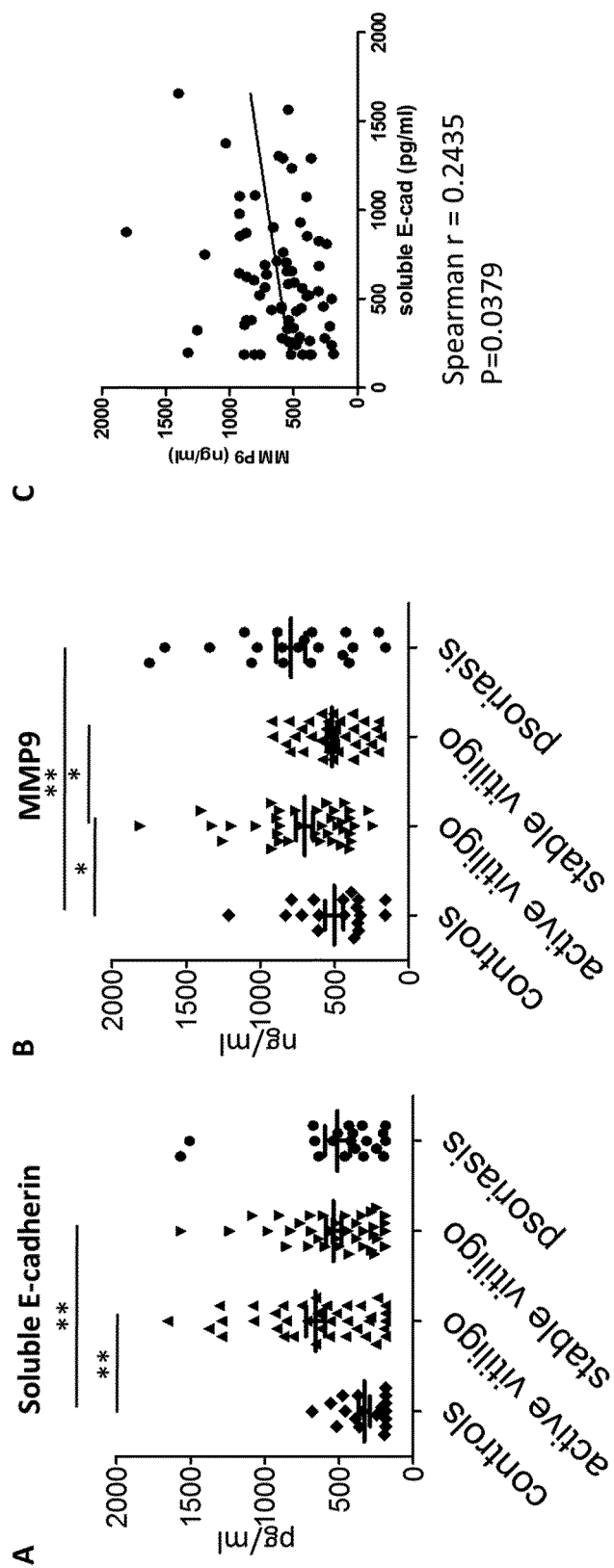

FIG. 9. MMP9 and soluble E-cadherin levels in vitiligo patient sera.

(A-B) Levels of soluble E-cadherin (A) and MMP9 (B) were determined by ELISA in the serum of patients with vitiligo (stable and progressive) or psoriasis, and in the serum of healthy controls. (C) Serum levels of MMP9 were correlated to serum levels of soluble E-cad in vitiligo patients (Spearman test p<0.05). Inventors show a significant increase of soluble E-cadherin and MMP9 levels in active and stable vitiligo patient's serum compared to healthy controls. Levels of MMP9 were significantly higher in vitiligo patients with active disease. In addition, a positive correlation was observed between MMP9 and soluble E-cadherin levels in vitiligo patients.

Figure 10:
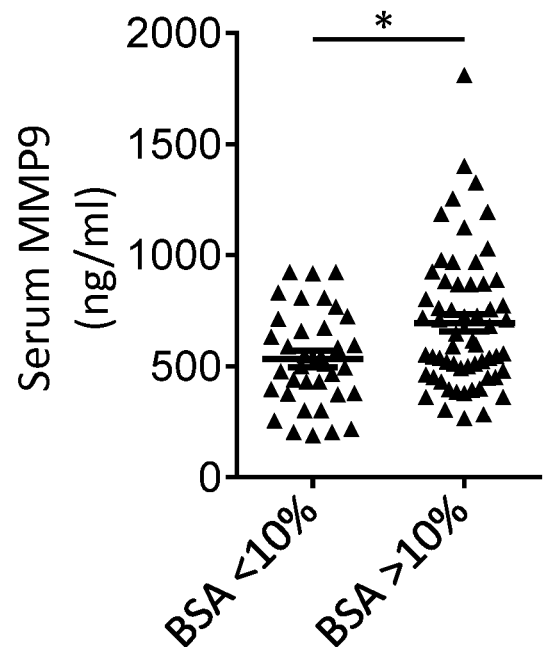
Figure 10:
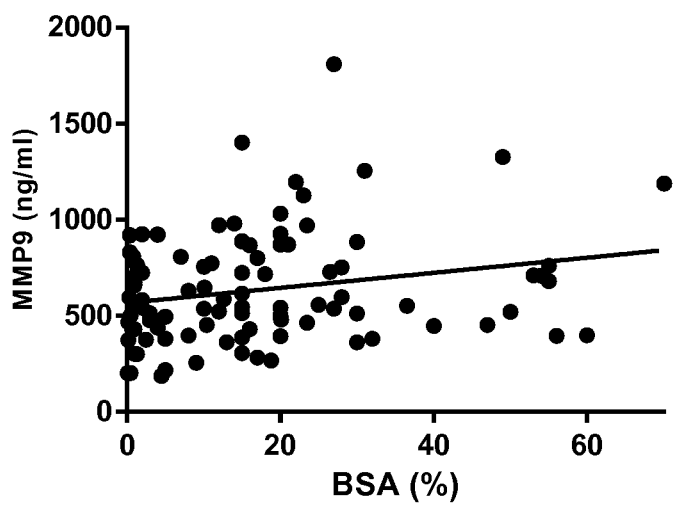

FIG. 10. Correlation of MMP9 levels in vitiligo patient sera with body surface area.

(A) Levels of MMP9 were determined by ELISA in the sera of patients with vitiligo (stable and progressive) and were classified based on the body surface area (BSA) involved (<10% or >10%). p<0.05, using a Mann Whitney test. (B) Serum levels of MMP9 were correlated to the body surface area (Spearman test p<0.05). A positive correlation is observed between MMP9 levels and the body surface area involved in vitiligo patients.

Figure 11:
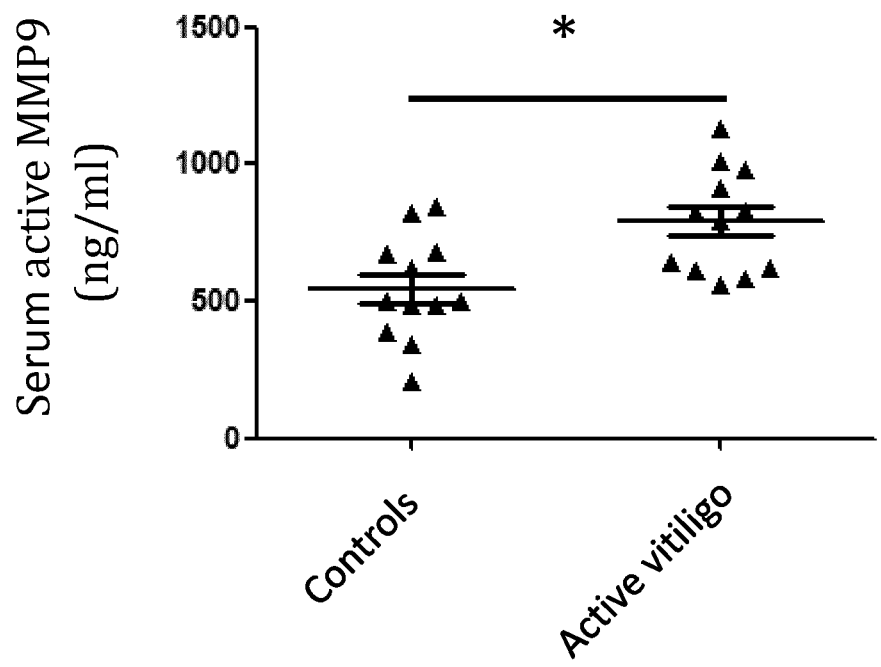

FIG. 11. Levels of active MMP9 in vitiligo patient sera.

Levels of active MMP9 were determined by using Fluorokine E human active MMP9 kit, in the sera of healthy controls (n=12) or patients with active vitiligo (n=12). Samples were activated with the addition of AMPA (p-aminophenyl mercuric acetate). p<0.05, using a Mann Whitney test. An increased expression of active MMP9 is observed in sera from active vitiligo patients.

Figure 12:
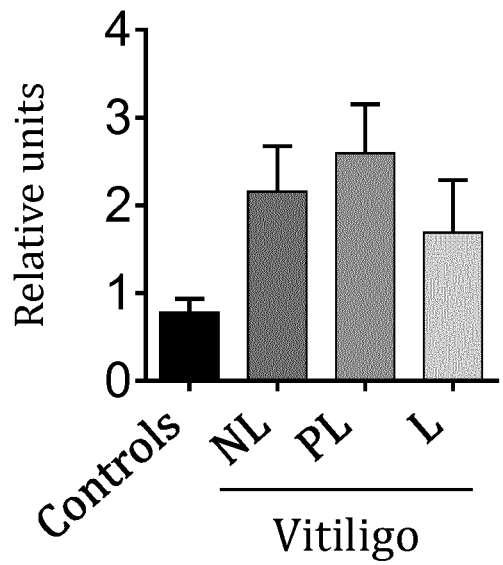
Figure 12:
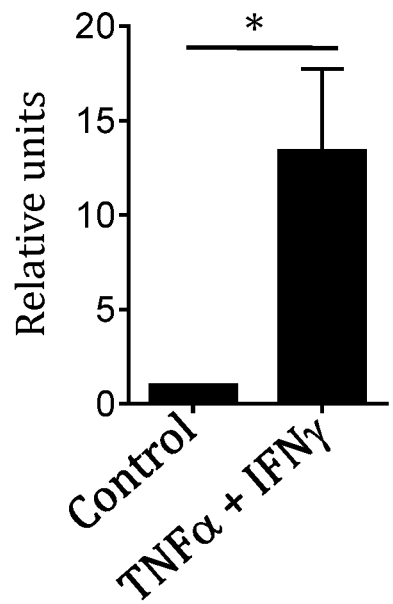

FIG. 12. MMP9 gene expression in skin and in a RHPE 3D model.

(A) MMP9 gene expression was assessed by real-time RT-PCR in healthy controls skin (n=6) and non lesional (NL), lesional (L), and perilesional (PL) skin of vitiligo patients (n=6). The mean+SEM is shown. (B) Reconstructed human pigmented epidermis were treated in the presence or absence of TNFα and IFNγ for 24 h. MMP9 gene expression was determined by real-time RT-PCR. P<0.01, using a Mann-Whitney test. An increased expression of MMP9 gene is observed in both lesional, perilesional, and non lesional skin of vitiligo patients compared to healthy skin from unaffected individuals. In addition, a TNFα and IFNγ induced MMP9 gene expression is shown using a RHPE 3D model.

Figure 13:
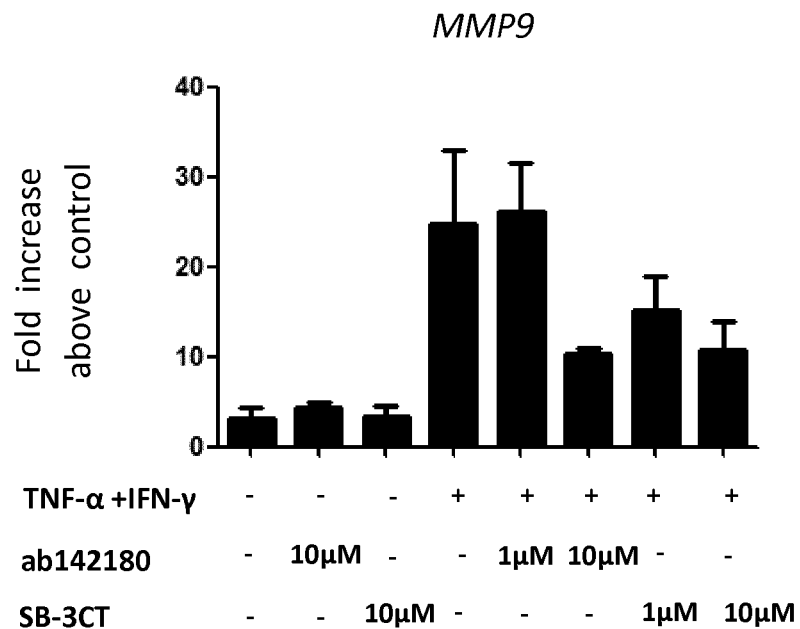
Figure 13:
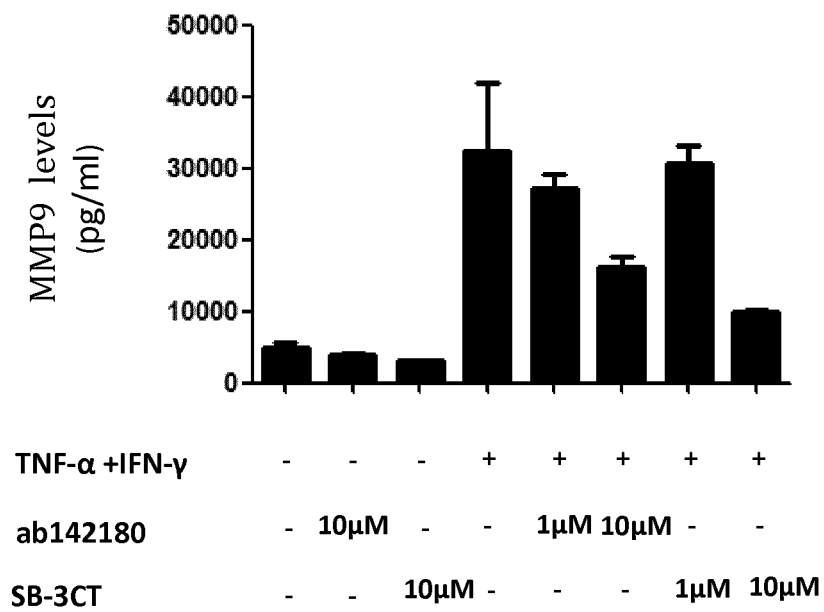

FIG. 13. Treatment of RHPE with or without TNFα and IFNγ in the presence or absence of MMP9 inhibitors ab142180 or SB-CT.

Reconstructed human pigmented epidermis were treated 24 h with or without 10 ng/ml of TNFα and IFNγ in the presence or absence of 1 μM and 10 μM of MMP9 inhibitors ab142180 or SB-CT. (A) Real-time PCR analysis of MMP9 gene expression. Results are expressed as a fold increase above control culture. GAPDH was used as a housekeeping gene. (B) Measurement of MMP9 levels by ELISA in cell-free supernatants. These results indicate that MMP9 inhibition reduces MMP9 production induced by the combination of TNFα and IFNγ.

EXAMPLES

1/Increased Secretion of TNFα and IFNγ by Skin Infiltrating T Cells in Vitiligo Inventors extracted T cells from perilesional skin of vitiligo patients with a stable or a progressive disease in order to analyze their propensity to produce inflammatory cytokines, in particular TNFα and IFNγ, two cytokines previously identified as potentially involved in disease development (reviewed in Boniface et al. G. Ital. Dermatol. Venereol 2016). Results were compared to those obtained from healthy individuals (FIG. 1). They show that CD4 and CD8 T cells extracted from the skin of vitiligo patients with active disease produce higher levels of the type-1 related cytokine IFNγ and TNFα, also known to be secreted by most of T cell subsets, suggesting their involvement in melanocyte loss.

2/TNFα and IFNγ: Two Major Cytokines Involved in Melanocyte Inhibition

Inventors next assessed the biological activities of pro- or anti-inflammatory cytokines on the expression of genes involved in melanocyte function, such as microphthalmia associated transcription factor (MITF, the melanocyte master transcription factor) and tyrosinase (TYR, involved in melanogenesis), as well as E-cadherin encoding gene (CDH1), a protein critical for melanocyte adhesion to keratinocytes and to the epidermis basal membrane. More precisely, they evaluated the effects of TNFα, IFNγ, IL-17, IL-1β, and TGFβ, alone or in combination, on primary cultures of human epidermal melanocytes (FIG. 2). IFNγ or TNFα inhibited the expression of genes involved in melanocyte differentiation, function, melanin synthesis, and melanocyte adhesion (FIG. 2A); TGFβ was also able to downregulate melanocyte function, although at a weaker level, whereas IL-17 and IL-1β had no or little effect. Strikingly, the combination of the 5 cytokines resulted in a robust inhibition of the studied genes. Inventors more specifically identified TNFα and IFNγ as the most potent cytokines that inhibit melanocyte function and adhesiveness (FIG. 2B).

3/TNFα and IFNγ Act Synergistically on Melanocytes to Inhibit Pigmentation and Induce Inflammatory Mediators Inventors evaluated the capability of TNFα and IFNγ to act in concert to modify melanocyte function. As shown in FIG. 3 and FIG. 6, TNFα and IFNγ synergized to downregulate the expression of genes involved in pigmentation signaling, such as MITF, the melanocyte master transcription factor, tyrosinase (TYR), and dopachrome tautomerase (DCT). TNFα and IFNγ also synergized to upregulate the expression of inflammatory genes in melanocytes, including IL-6, TNFα, and intercellular adhesion molecule-1 (ICAM-1), and they also induced production of the CXCR3 ligands CXCL9 and CXCL10 (FIG. 3B). These results reveal for the first time that a melanocyte can become an inflammatory cell under the influence of type-1-related cytokines and could amplify the inflammatory response observed in vitiligo.

4/TNFα And IFNγ Induce Melanocyte Detachment Through E-Cadherin Alteration and Induction of MMP9

Inventors showed that TNFα and IFNγ have a synergistic effect to downregulate the expression of CDH1 transcripts in melanocytes (FIG. 4A), but not in keratinocytes (FIG. 4B). Such effects are of interest as E-cadherin, which is the major mediator of human melanocytes adhesion, was recently shown to be discontinuously distributed across melanocyte membranes of vitiligo patients (Wagner et al. J Invest Dermatol. 2015). E-cadherin is a transmembrane protein existing in two forms: the full length E-cadherin and soluble E-cadherin (David et al. Cancer Res 2012). The soluble form has been shown to be upregulated in the sera of patients with autoimmune diseases (Jin et al. J Rheumatol 2013; Matsuoyoshi et al. Br J Dermatol 1995). Inventors determined the levels of soluble E-cadherin in sera of vitiligo patients. As shown in FIG. 4C, levels of soluble E-cadherin were significantly higher in vitiligo patients compared to healthy controls. In addition, such levels tend to correlate with disease activity and indicate that levels of soluble E-cadherin can be used as a marker for disease activity. Several enzymes can cleave full length E-cadh and lead to the release of its soluble form, including matrix metalloproteinase MMP9 (aka gelatinase) (Symowicz et al. Cancer Res 2007). Inventors showed that both total MMP9 and active MMP9 levels were significantly higher in serum of patients with vitiligo than in healthy controls (FIGS. 8 and 11). MMP9 levels were significantly higher in patients with active disease compared to stable vitiligo. Strikingly, they observed a positive correlation between MMP9 and soluble E-cadherin levels in vitiligo patients. A positive correlation between MMP9 levels and the body surface area involved in vitiligo patients was also observed (FIG. 10). They also showed an increased expression of MMP9 gene in both lesional, perilesional, and non lesional skin of vitiligo patients compared to healthy skin from unaffected individuals (FIG. 12A). Importantly, inventors showed that TNFα upregulated expression of MMP9 gene in melanocytes (FIG. 4D); such effect was potentiated in the presence of IFNγ. These results suggest that MMP9 could be involved in the up-regulation of soluble E-cadherin in vitiligo.

Next, to better characterize the biological activities of TNFα and IFNγ on melanocyte adhesion, inventors used an in vitro 3D cellular model of depigmentation containing both melanocytes and keratinocytes. Strikingly, they demonstrated that the combined activities of TNFα and IFNγ induce melanocyte detachment from the model basal layer, at least in part mediated through alteration of E-cadherin expression (FIG. 4E) and upregulation of MMP9 gene expression (FIG. 12B). A decrease in DCT, a melanogenesis-associated gene, was also observed (FIG. 7). Such phenotype clearly resembles the one observed in perilesional skin of vitiligo patients (with a stable or a progressive disease), where melanocytes are detached from the basal layer of the epidermis (FIG. 4F). Interestingly, such phenomenon is also observed in psoriasis (FIG. 4F), emphasizing that melanocyte adhesion defect can be extended to other skin inflammatory conditions like psoriasis. Moreover, the inventors showed that TNFα and IFNγ, alone or in combination, have little or no effect on melanocyte apoptosis (FIG. 8A). These data are in line with the observation that melanocyte do not undergo apoptosis in vitiligo patients perilesional skin (FIG. 8B), emphasizing that melanocyte detachment is the primary mechanism involved in melanocyte loss in vitiligo. Altogether, these results are of major interest and identify a new mechanism leading to melanocyte loss, with a critical role of TNFα and IFNγ. In addition, this in vitro model of depigmentation can advantageously be used to test new therapeutic targets in vitiligo patients, as well as in patients with depigmenting disorders associated with inflammatory skin diseases.

5/MMP9 Inhibition Prevents TNFα and IFNγ-Induced Depigmentation Through Melanocyte Stabilisation to the Basal Membrane of the Epidermis As discussed above, TNFα and IFNγ induce MMP9 gene expression in melanocyte. Inventors used two commercially available synthetic MMP9 inhibitors, SB3CT (a non-selective MMP2 and MMP3 inhibitor) and a selective MMP9 inhibitor (ab142180), to assess whether such inhibition could inhibit TNFα and IFNγ effects on depigmentation. In vitro reconstructed human epidermis containing melanocytes were stimulated with these two cytokines in the presence or absence of the two different MMP9 inhibitors for 24 h (FIG. 5). The combination of TNFα and IFNγ induced melanocyte detachment and E-cadherin inhibition. Importantly, such effect was strongly inhibited in the presence of either MMP9 inhibitor, as MMP9 inhibition led to melanocyte stabilisation to the basal membrane of the epidermis (FIG. 5) and reduced MMP9 expression induced by the combination of IFNγ and TNFα both at the gene and protein levels (FIG. 13). These results are the first to demonstrate that IFNγ and TNFα effect on melanocyte adhesion is mediated through MMP9.

All together, these results support the concept that inhibiting MMP9 represent an attractive and novel strategy to prevent melanocyte loss in vitiligo, but also in depigmentation occurring in skin inflammatory disorders such as psoriasis, atopic dermatitis, scleroderma or hypomelanosis.

6/Example of a Method of Preparing a Reconstructed Depigmented Melanized Epidermis Model Pigmented epidermis (RHEm) are reconstructed from normal human keratinocytes (NHEK) and from normal human melanocytes (NHEM), previously isolated from preputial samples.

1. RHEm Treatments

After 10 days of reconstruction (D10), reconstructed human pigmented epidermis (RHEm) are placed in 6 wells plate (NUNC reference 140675) in 2 ml of culture medium without hydrocortisone to which 10 ng/ml of interferon (IFN)-γ (R&D systems) and 10 ng/ml of "tumor necrosis factor (TNF)-α" (R&D systems) are added. A control condition without cytokines addition is performed. Each experimental condition is performed in duplicate or triplicate.

Composition of the culture medium without hydrocortisone: complete EpiLife® Medium (cascade Biologics® base medium reference M-EPI-500-CA+supplements reference S-001-K among which IGF-1 and hydrocortisone aliquots have not been used) supplemented with:
  5 μg/ml of bovine insulin (Sigma Aldrich 11882)
  50 μg/ml of vitamin C (Sigma Aldrich A4403)
  3 ng/ml of keratinocyte growth factor (KGF) (Millipore GF008)
  1.5 mM of CaCl$_2$ (Sigma Aldrich C7902).

After a 24 h incubation period, the inserts containing the reconstructed epidermis are collected with a plier, left on a towel in order to remove residual liquid under the insert, then the reconstructed epidermis were cut from the support with a scalpel, put in a formaldehyde solution before dehydration, and then embedded in paraffin.

2. Analysis of Melanocytes Detachment

5 μm sections of paraffin inclusions are deposited on slides for labelling by immunofluorescence to reveal MelanA and E-Cadherin according to the following protocol:

| | | |
|---|---|---|
| 1- | Deparaffinization | |
| | Placing the slides on a hot plate at 70° C. | 10 min |
| | Successive xylene baths | 3 × 5 min |
| 2- | Hydration | |
| | Ethanol 100° | 1 min |
| | Ethanol 100° | 1 min |
| | Ethanol 95° | 1 min |
| | Ethanol 70° | 1 min |
| | Ethanol 50° | 1 min |
| | Distilled water | 1 min |
| | PBS or TBS | 5 min |
| 3- | Antigen accessibility | |
| | Use of the Decloacking Chamber device BIOCARE Medical | |
| | Place the slides into the device at pH 8 | |
| | Launch the program (98° C. - 20 min) | |
| | Wash with TBS (Tris buffer saline) 0.1% Tween at a temperature equal to cooling temperature (60-70° C.). | |
| | Allow to come back to room temperature | |
| 4- | Wash with TBS 0.1% tween | 3 × 5 min |
| 5- | Delimit the deposition areas with a hydrophobic pen | |
| 6- | Put the primary anti-MELANAA antibody (1) at 1/100 dilution and the anti-E-CADHERIN antibody (2) at 1/100 dilution in the buffer (3) Incubate overnight at 4° C. | |
| 7- | The day after: wash with TBS 0.1% tween | 3 × 5 min |
| | Put the secondary antibody A555 (4) at 1/100 dilution in the buffer (3) + A 488 (5) at 1/100 dilution in the buffer (3) | 60 min |
| 8- | Wash with TBS 0.1% tween | 3 × 5 min |

Assemble slide with medium assembly with "DAPI" (6) away from light.
  (1): DAKO Melan-A Clone A103 Isotype IgG1, Kappa (ref: M 7196)
  (3): DAKO Antibody Diluent with background reducing components (ref: S3022)
  (2): Abcam rabbit anti-E-cadherin antibody (ref: ab 15148)
  (4): Invitrogen Alexa 555 goat anti mouse IgG (ref: A21422)
  (5): Invitrogen Alexa 488 rabbit IgG(H+L) (ref: A21441) or Novus (ref: NBP 1-72944) (6): Molecular Probes Prolong gold antifade reagent with DAPI (ref: P36935)

Then reading with a fluorescence microscope for the analysis of melanocytes detachment.

Conclusion: Inventors herein identify inhibitors of matrix metalloproteinase-9 (MMP9) as active molecules for use for preventing, treating or alleviating depigmenting disorders, typically depigmenting disorders associated with inflammation, in a subject in need thereof. Such molecules are of particular interest for preventing, treating or alleviating vitiligo, leukotrichia, psoriasis, atopic dermatitis, scleroderma and hypomelanosis.

REFERENCES

Boniface K, Taieb A, Seneschal J. New insights into immune mechanisms of vitiligo. G. Ital. Dermatol. Venereol. 2016; 151(1):44-54.

David J M, Rajasekaran A K. Dishonorable discharge: the oncogenic roles of cleaved E-cadherin fragments. Cancer Res 2012; 72: 2917-23.

Ezzedine K et al. Vitiligo is not a cosmetic disease. JAAD 2015; 73(5):883-5

Jin T et al. Soluble E-cadherin in systemic lupus erythematosus. J Rheumatol 2013; 40: 1677-82.

Matsuyoshi N et al. Soluble E-cadherin: a novel cutaneous disease marker. Br J Dermatol 1995; 132: 745-9.

Natarajan V T et al. IFN-γ signaling maintains skin pigmentation homeostasis through regulation of melanosome maturation. Proc Natl Acad Sci USA. 2014; 111:2301-6.

Symowicz, J. et al. Engagement of collagen-binding integrins promotes matrix metalloproteinase-9-dependent E-cadherin ectodomain shedding in ovarian carcinoma cells. *Cancer Res.* 67,2030-2039 (2007).

Taïeb A, Picardo M. Clinical practice. Vitiligo. N Engl J Med. 2009; 360:160-9.

Wagner R Y, et al. Altered E-Cadherin Levels and Distribution in Melanocytes Precede Clinical Manifestations of Vitiligo. J Invest Dermatol. 2015 July; 135(7):1810-9.

Wang C Q F et al. IL-17 and TNF synergistically modulate cytokine expression while suppressing melanogenesis: potential relevance to psoriasis. J Invest Dermatol. 2013; 133:2741-52.

Wang S et al. Interferon-γ induces senescence in normal human melanocytes. PloS One. 2014; 9:e93232.

Webb K C et al. Tumour necrosis factor-α inhibition can stabilize disease in progressive vitiligo. Br J Dermatol. 2015; 173:641-50.

Whitton, M. E. et al. Interventions for vitiligo. Cochrane Database Syst Rev CD003263 (2010).

Yang L et al. Interferon-gamma Inhibits Melanogenesis and Induces Apoptosis in Melanocytes: A Pivotal Role of CD8+Cytotoxic T Lymphocytes in Vitiligo. Acta Derm Venereol. 24 juin 2015; 95(6):664-70.

The invention claimed is:

1. A method for treating or alleviating a depigmenting disorder in a subject in need thereof, comprising a step of administering an inhibitor of matrix metalloproteinase-9 (MMP9) or a composition comprising an inhibitor of MMP9, to the subject.

2. The method according to claim 1, wherein the inhibitor stabilizes melanocytes to the basement membrane of the epidermis.

3. The method according to claim 1, wherein the inhibitor is selected from an antibody, an aptamer, a spiegelmer, an inhibitory nucleic acid sequence, 2-[[(4-phenoxyphenyl)sulfonyl]methyl]-thiirane, 2-(N-benzyl-4-methoxyphenylsulfonamido)-5-((diethylamino)methyl)-N-hydroxy-3-methylbenz amide, and N-{2-[(2-methoxyphenyl)amino]-4'-methyl-4,5'-bi-1,3-thiazol-2'-yl}acetamide.

4. The method according to claim 3, wherein the inhibitor is selected from the group consisting of an anti-MMP9 antibody comprising a heavy chain variable region comprising SEQ ID NO: 2, 3 or 4, and/or a light chain comprising SEQ ID NO: 5, GS-5745 (Andecaliximab) and CALY-001.

5. The method according to claim 1, wherein the depigmenting disorder is associated with an inflammatory skin disease.

6. The method according to claim 5, wherein the inflammatory skin disease is selected from vitiligo, psoriasis, atopic dermatitis, scleroderma, hypomelanosis and leukotrichia.

7. The method according to claim 1, wherein the depigmenting disorder or inflammatory skin disease is vitiligo.

8. The method according to claim 1, wherein the composition is used alone or in combination with phototherapy or with a drug selected from a Janus kinase (JAK) inhibitor and a calcineurin inhibitor.

9. The method according to claim 1, wherein the subject is a human being.

10. The method according to claim 3, wherein the inhibitor is selected from 2-[[(4-phenoxyphenyl)sulfonyl]methyl]-thiirane, 2-(N-benzyl-4-methoxyphenylsulfonamido)-5-((diethylamino)methyl)-N-hydroxy-3-methylbenz amide, and N-{2-[(2-methoxyphenyl)amino]-4'-methyl-4,5'-bi-1,3-thiazol-2'-yl}acetamide.

11. The method according to claim 10, wherein the inhibitor is 2-(N-benzyl-4-methoxyphenylsulfonamido)-5-((diethylamino)methyl)-N-hydroxy-3-methylbenz amide.

12. The method according to claim 10, wherein the inhibitor is 2-[[(4-phenoxyphenyl)sulfonyl]methyl]-thiirane.

13. The method according to claim 10, wherein the inhibitor is N-{2-[(2-methoxyphenyl)amino]-4'-methyl-4,5'-bi-1,3-thiazol-2'-yl}acetamide.

14. The method according to claim 1, wherein the steop of administering an inhibitor of matrix metall metalloproteinase-9 (MMP9) or a composition thereof is administered topically.

15. The method accordding to claim 1, wherein the inhibitor of matrix metalloproteinase-9 (MMP9) or a composition thereof is administered cutaneously or subcutaneously.

* * * * *

UNITED STATES PATENT AND TRADEMARK OFFICE
CERTIFICATE OF CORRECTION

| | | |
|---|---|---|
| PATENT NO. | : 10,894,837 B2 | Page 1 of 1 |
| APPLICATION NO. | : 16/469665 | |
| DATED | : January 19, 2021 | |
| INVENTOR(S) | : Boniface et al. | |

It is certified that error appears in the above-identified patent and that said Letters Patent is hereby corrected as shown below:

In the Specification

Column 2,
Line 65, "to to," should read --to t0,--.

Column 16,
Line 38, "IL-113," should read --IL-1β,--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 5

<210> SEQ ID NO 1
<211> LENGTH: 707
<212> TYPE: PRT
<213> ORGANISM: Homo sapiens

<400> SEQUENCE: 1

Met Ser Leu Trp Gln Pro Leu Val Leu Val Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
                180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
    275                 280                 285

Gln Phe Pro Phe Ile Phe Gln Gly Gln Ser Tyr Ser Ala Cys Thr Thr
                290                 295                 300
```

```
Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
            325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
            405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
            485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
            565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
            645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
            690                 695                 700

Pro Glu Asp
705
```

```
<210> SEQ ID NO 2
<211> LENGTH: 116
<212> TYPE: PRT
<213> ORGANISM: Artificial Sequence
<220> FEATURE:
<223> OTHER INFORMATION: Heavy chain (G03-VH-GL)

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Gly Met Asp Val Trp Gly Gln Gly Thr Thr Val
                100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Heavy chain (G03-VH-GL-V1)

<400> SEQUENCE: 3

Glu Val Gln Leu Val Gln Ser Gly Ala Glu Val Lys Lys Pro Gly Ala
1               5                   10                  15

Ser Val Lys Val Ser Val Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Tyr Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Gly Met Asp Val Trp Gly Gln Gly Thr Thr Val
                100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Heavy chain (G03-VH-GL-V1-V9)

<400> SEQUENCE: 4

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Tyr Ile Ser Ala Tyr Asn Ala Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Gly Met Asp Val Trp Gly Gln Gly Thr Thr Val
            100                 105                 110

Thr Val Ser Ser
        115

<210> SEQ ID NO 5
<211> LENGTH: 108
<212> TYPE: PRT
<213> ORGANISM: Artificial Sequence
<220> FEATURE:
<223> OTHER INFORMATION: Light chain (G06-VL-GL1c)

<400> SEQUENCE: 5

Gln Ala Val Leu Thr Gln Pro Pro Ser Ala Ser Gly Thr Pro Gly Gln
1               5                   10                  15

Arg Val Thr Ile Ser Cys Ser Gly Ser Thr Phe Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asp Ser His Arg Pro Ser Gly Val Pro Asp Arg Phe Ser
    50                  55                  60

Gly Ser Asn Ser Trp Asn Thr Ala Ser Leu Ala Ile Ser Gly Leu Gln
65                  70                  75                  80

Ser Glu Asp Glu Ala Asp Tyr Tyr Cys Gln Ala Trp Asp Ser Ser Ala
                85                  90                  95

Val Val Phe Gly Gly Gly Thr Lys Val Thr Val Leu
            100                 105
```